United States Patent
Bourke, Jr. et al.

(10) Patent No.: US 9,488,916 B2
(45) Date of Patent: Nov. 8, 2016

(54) INTERIOR ENERGY-ACTIVATION OF PHOTO-REACTIVE SPECIES INSIDE A MEDIUM OR BODY

(71) Applicant: IMMUNOLIGHT, LLC., Detroit, MI (US)

(72) Inventors: Frederic Avery Bourke, Jr., Greenwich, CT (US); Zakaryae Fathi, Raleigh, NC (US); Harold Walder, Belville, NC (US); Wayne F. Beyer, Jr., Bahama, NC (US)

(73) Assignee: IMMUNOLIGHT, LLC., Detroit, MI (US)

( * ) Notice: Subject to any disclaimer, the term of this patent is extended or adjusted under 35 U.S.C. 154(b) by 261 days.

(21) Appl. No.: 14/206,337

(22) Filed: Mar. 12, 2014

(65) Prior Publication Data

US 2014/0272030 A1   Sep. 18, 2014

Related U.S. Application Data

(60) Provisional application No. 61/792,125, filed on Mar. 15, 2013.

(51) Int. Cl.
*G03F 7/20* (2006.01)
*A23L 3/26* (2006.01)
(Continued)

(52) U.S. Cl.
CPC ............... *G03F 7/20* (2013.01); *A23L 3/263* (2013.01); *A23L 3/28* (2013.01); *A61L 2/0041* (2013.01); *A61L 2/0047* (2013.01); *A61L 2/08* (2013.01); *A61L 2/082* (2013.01); *A61M 1/3681* (2013.01); *A61N 5/062* (2013.01); *C02F 1/32* (2013.01); *C02F 1/325* (2013.01);
*A61L 2202/24* (2013.01); *A61M 1/3683* (2014.02); *A61N 5/0624* (2013.01); *A61N 2005/0661* (2013.01);
(Continued)

(58) Field of Classification Search
USPC ........................................... 250/492.1, 492.2
See application file for complete search history.

(56) References Cited

U.S. PATENT DOCUMENTS

2002/0183301 A1   12/2002   Rychnovsky
2009/0294692 A1   12/2009   Bourke, Jr. et al.
(Continued)

FOREIGN PATENT DOCUMENTS

WO   WO 2013/009688 A1   1/2013

OTHER PUBLICATIONS

Combined International Search Report and Written Opinion with Search History issued Aug. 22, 2014 in PCT/US14/27965.
(Continued)

*Primary Examiner* — Kiet T Nguyen
(74) *Attorney, Agent, or Firm* — Oblon, McClelland, Maier & Neustadt, L.L.P.

(57) ABSTRACT

A method and a system for producing a change in a medium. The method places in a vicinity of the medium an energy modulation agent. The method applies an initiation energy to the medium. The initiation energy interacts with the energy modulation agent to directly or indirectly produce the change in the medium. The energy modulation agent has a normal predominant emission of radiation in a first wavelength range outside of a second wavelength range (WR2) known to produce the change, but under exposure to the applied initiation energy produces the change. The system includes an initiation energy source configured to apply an initiation energy to the medium to activate the energy modulation agent.

66 Claims, 19 Drawing Sheets

(51) Int. Cl.
- *A23L 3/28* (2006.01)
- *A61L 2/08* (2006.01)
- *A61M 1/36* (2006.01)
- *C02F 1/32* (2006.01)
- *A61N 5/06* (2006.01)
- *A61L 2/00* (2006.01)
- *C02F 1/30* (2006.01)

(52) U.S. Cl.
CPC ........ *A61N2005/0662* (2013.01); *C02F 1/307* (2013.01); *C02F 2201/32* (2013.01); *C02F 2305/10* (2013.01); *Y02W 10/37* (2015.05)

(56) References Cited

U.S. PATENT DOCUMENTS

| | | |
|---|---|---|
| 2010/0261263 A1 | 10/2010 | Vo-Dinh et al. |
| 2011/0117202 A1* | 5/2011 | Bourke, Jr. ........ H05B 41/2806 424/490 |
| 2012/0089180 A1 | 4/2012 | Fathi et al. |

OTHER PUBLICATIONS

U.S. Appl. No. 14/168,795, filed Jan. 30, 2014, Vo-Dinh, et al.
U.S. Appl. No. 14/245,668, filed Apr. 4, 2014, Bourke.

* cited by examiner

| ENDOGENOUS FLUOROPHORES | EXCITATION MAX. (nm) | EMISSION MAX. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325,360 | 400 |
| Elastin | 290,325 | 405 |
| Enzymes and Coenzymes: | | |
| flavins adenine dinucleotide | 450 | 535 |
| reduced nicotinamidedinucleotide | 290,351 | 440,460 |
| reduced nicotinamide dinucleotide phosphate | 336 | 464 |
| Vitamins: | | |
| Vitamin A | 327 | 510 |
| Vitamin K | 335 | 480 |
| Vitamin D | 390 | 480 |
| Vitamins B$_6$ compounds: | | |
| Pyridoxine | 332,340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin B$_{12}$ | 275 | 305 |
| Lipids: | | |
| Phospholipids | 436 | 540,560 |
| Lipofuscin | 340-395 | 540,430-460 |
| Ceroid | 340-395 | 430-460,540 |
| Porphyrins | 400-450 | 630,690 |

*Fig. 2*

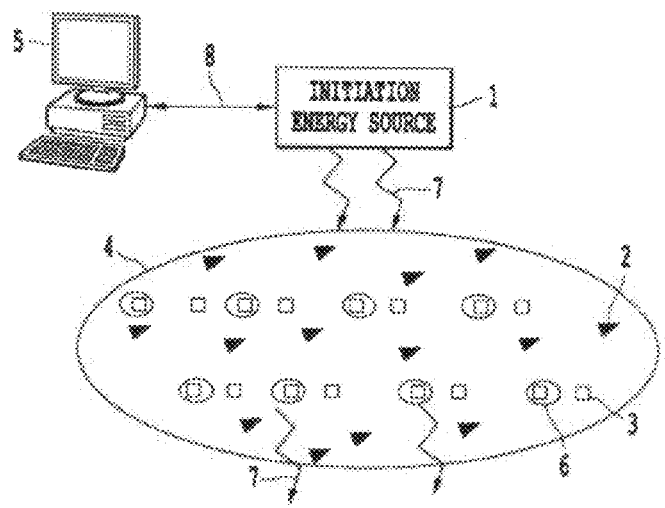

*Fig. 3A*

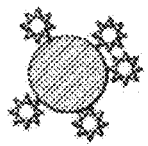
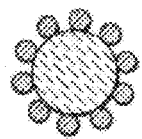

PA MOLECULES BOUND TO METAL NANOPARTICLE

*Fig. 6A*

PA-CONTAINING NANO-PARTICLE COVERED WITH METAL NANOPARTICLES

*Fig. 6B*

☼ PHOTO-ACTIVE (PA) MOLECULE (PHOTOSENSITIZER)

▨ METAL (e.g. Au, Ag)

▩ MATERIAL CONTAINING PA

▦ PROTECTIVE COATING

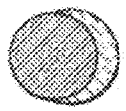
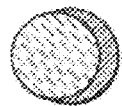

METAL NANOPARTICLE COVERED WITH PA NANOCAP

*Fig. 6C*

PA-CONTAINING NANO-PARTICLE COVERED WITH METAL NANOCAP

*Fig. 6D*

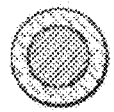
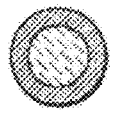
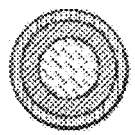

METAL NANOPARTICLE COVERED WITH PA NANOSHELL

*Fig. 6E*

PA-CONTAINING NANO-PARTICLE COVERED WITH METAL NANOSHELL

*Fig. 6F*

PA-CONTAINING NANO-PARTICLE COVERED WITH METAL NANOSHELL WITH PROTECTIVE COATING LAYER

*Fig. 6G*

NANOPARTICLE IMPROVES DELIVERY OF PA MOLECULES INTO TARGET DISEASED CELLS

INTERIOR ENERGY-ACTIVATION OF PHOTO-REACTIVE SPECIES INSIDE A MEDIUM OR BODY

CROSS REFERENCE TO RELATED APPLICATIONS

This application claims priority to U.S. provisional application No. 61/792,125 filed on Mar. 15, 2013, the entire contents of which are incorporated herein by reference. U.S. provisional application No. 61/792,125 is related to provisional U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to U.S. Ser. No. 13/102,277 entitled "ADHESIVE BONDING COMPOSITION AND METHOD OF USE," filed May 6, 2011, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 12/389,946, filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655, filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to and claims priority under 35 U.S.C. 119(e) to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to and claims priority under 35 U.S.C. 119(e) to provisional Ser. No. 61/080,140, filed Jul. 11, 2008, entitled "PLASMONIC ASSISTED SYSTEMS AND METHODS FOR INTERIOR ENERGY-ACTIVATION FROM AN EXTERIOR SOURCE," the entire contents of which are hereby incorporated herein by reference.

BACKGROUND OF THE INVENTION

1. Field of Invention

The invention relates to methods and systems for generating in the interior of a medium or body radiant energy for producing a change in the properties of a medium or body by exposure to the radiation.

2. Discussion of the Background

Presently, light (i.e., electromagnetic radiation from the radio frequency through the visible to the x-ray and gamma ray wavelength range) activated processing is used in a number of industrial processes ranging from photoresist curing, to on-demand ozone production, to sterilization, to the promotion of polymer cross-linking activation (e.g. in adhesive and surface coatings) and others. Today, light activated processing is seen in these areas to have distinct advantages over more conventional approaches. For example, conventional sterilization by steam autoclaving or in food processing by pasteurization may unsuitably overheat the medium to be sterilized. As such, light activated curable coatings are one of the fastest growing sectors in the coatings industry. In recent years, this technology has made inroads into a number of market segments like fiber optics, optical and pressure-sensitive adhesives, and automotive applications like cured topcoats, and curable powder coatings. The driving force of this development is mostly the quest for an increase in productivity of the coating and curing process, as conventional non light activated adhesive and surface coatings typically require 1) the elimination of solvents from the adhesive and surface coatings to produce a cure and 2) a time/temperature cure which adds delay and costs to the manufacturing process.

Moreover, the use of solvent based products in adhesive and surface coatings applications is becoming increasingly unattractive because of rising energy costs and stringent regulation of solvent emissions into the atmosphere. Optimum energy savings as well as beneficial ecological considerations are both served by radiation curable adhesive and surface coating compositions. Radiation curable polymer cross-linking systems have been developed to eliminate the need for high oven temperatures and to eliminate the need for expensive solvent recovery systems. In those systems, light irradiation initiates free-radical cross-linking in the presence of common photo sensitizers.

However, in the adhesive and surface coating applications and in many of the other applications listed above, the light-activated processing is limited due to the penetration depth of light into the processed medium. For example, in water sterilization, ultraviolet light sources are coupled with agitation and stirring mechanisms in order to ensure that any bacteria in the water medium will be exposed to the UV light. In light-activated adhesive and surface coating processing, the primary limitation is that the material to be cured must be directly exposed to the light, both in type (wavelength or spectral distribution) and intensity. In adhesive and surface coating applications, any "shaded" area will require a secondary cure mechanism, increasing cure time over the non-shaded areas and further delaying cure time due to the existent of a sealed skin through which subsequent curing must proceed (i.e., referred to as a cocoon effect).

SUMMARY OF THE INVENTION

The invention overcomes the problems and disadvantages of the prior art as described in the various embodiments below.

In one embodiment, there is provided a method for producing a change in a medium or body. The method includes (1) placing in a vicinity of the medium or body at least one energy modulation agent configured to emit radiation into the medium or body upon interaction with an initiation energy and (2) applying the initiation energy from an energy source to the medium or body. The applied initiation energy interacts with the energy modulation agent to directly or indirectly produce the change in the medium or body by the emitted radiation. The energy modulation agent has a normal predominant emission of radiation in a first wavelength range (WR1) outside of a second wavelength range (WR2) known to produce the change, but under exposure to the applied initiation energy produces the change.

In another embodiment, there is provided a method for curing of a radiation-curable medium. The method includes applying an initiation energy throughout a composition comprising 1) an uncured radiation-curable medium and 2) at least one energy modulation agent. The initiation energy interacts with the energy modulation agent to directly or indirectly cure the uncured medium by polymerization of polymers in the medium. The method includes curing the radiation-curable medium by activating a photoinitiator in the radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

In another embodiment, there is provided a system for producing a change in a medium disposed in an artificial container. The system includes a mechanism configured to provide to the medium 1) an activatable agent and 2) at least one energy modulation agent, The energy modulation agent is configured to emit light into the medium upon interaction with an initiation energy. The system includes an initiation energy source configured to apply the initiation energy to the medium. The energy modulation agent has a normal predominant emission of radiation in a first wavelength range (WR1) outside of a second wavelength range (WR2) known to produce the change, but under exposure to the applied initiation energy produces the change.

In another embodiment, there is provided a system for curing of a radiation-curable medium. The system includes 1) a mechanism configured to supply an uncured radiation-curable medium including an activatable agent and at least one energy modulation agent into the uncured radiation-curable medium and 2) an initiation energy source configured to apply an initiation energy throughout a region including the uncured radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

In another embodiment, there is provided a radiation-curable article including a radiation-curable medium and at least one energy modulation agent distributed throughout the medium. The energy modulation agent being a substance which is capable of converting initiation energy to a light capable of curing the radiation-curable medium by polymerization of polymers in the radiation-curable medium. The energy modulation agent has a normal predominant emission of radiation in a first wavelength range (WR1) outside of a second wavelength range (WR2) known to cure the radiation-curable medium, but under exposure to the applied initiation energy cures the radiation-curable medium.

In another embodiment, there is provided a method for producing a patterned element inside a structure. The method included (1) placing inside the structure a radiation curable medium including at least one energy modulation agent, with the energy modulation agent configured to emit light into the medium upon interaction with an initiation energy, and (2) applying to the medium the initiation energy from a directed or focused energy source. The energy modulation agent has a normal predominant emission of radiation in a first wavelength range (WR1) outside of a second wavelength range (WR2) known to radiation curable medium, but under exposure to the applied initiation energy cures the radiation curable medium and produces the patterned element inside the structure.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 2 is a table providing a list of possible, but not comprehensive, photoactivatable agents;

FIG. 3A is a schematic depicting a system according to one embodiment of the invention in which an initiation energy source is directed to a self-contained medium for producing changes in the medium;

FIGS. 6A-6G provide representative embodiments of plasmonics photo-active probes useful in the invention;

FIGS. 7A and 7B are graphical explanations of the plasmonics-enhanced effect of the invention;

FIGS. 8A-8J show representative embodiments of plasmonics-active nanostructures;

DETAILED DESCRIPTION OF THE INVENTION

Figure 1:
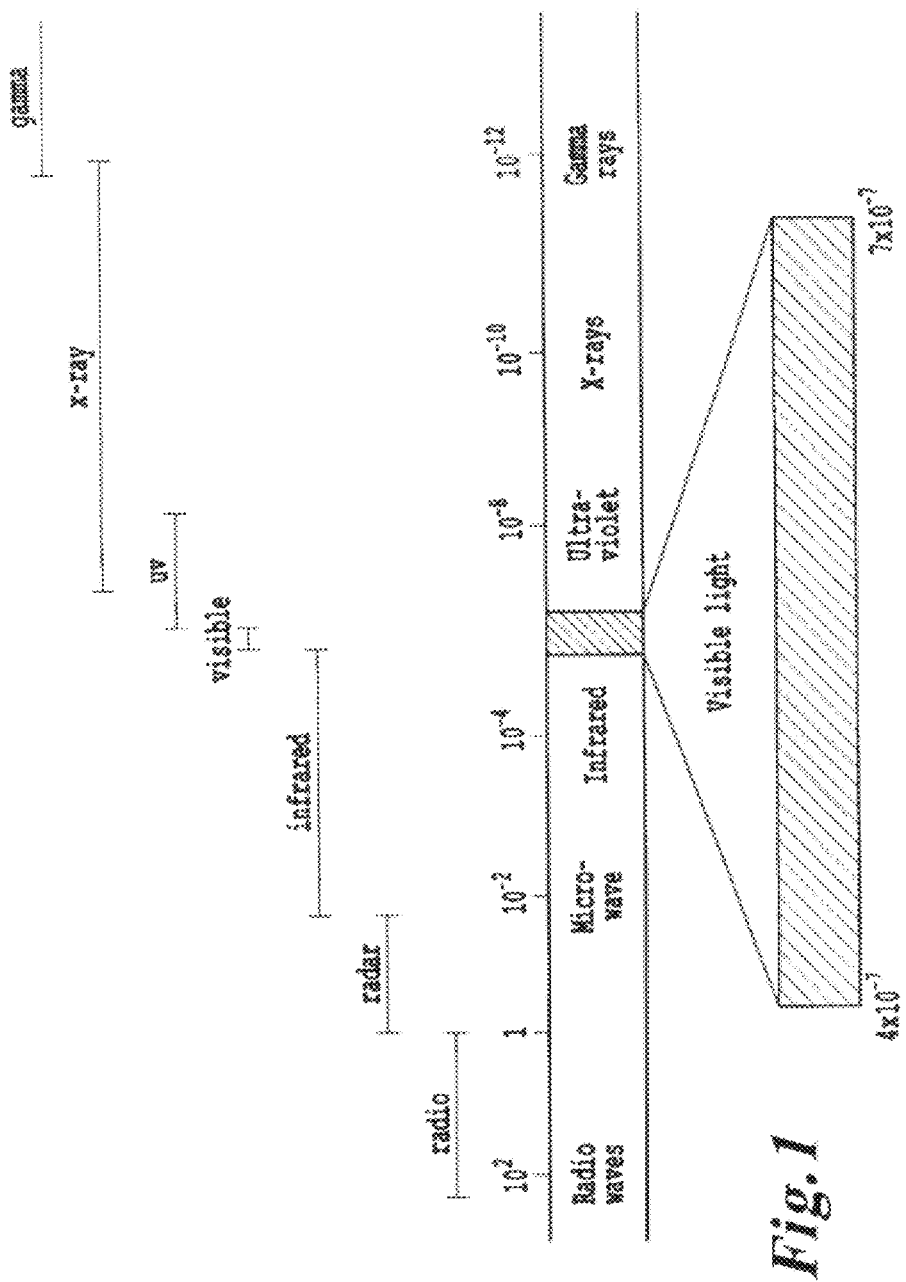
FIG. 1 provides an exemplary electromagnetic spectrum in meters (1 nm equals $10^{-9}$ meters)

The invention sets forth a novel method for causing a change in activity of an in a medium or body that is effective, specific, and able to produce a change to the medium or body. The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

In one embodiment, the present invention provides a method for producing a change in a medium or body, comprising:

(1) placing in a vicinity of the medium or body at least one energy modulation agent configured to emit radiation into the medium or body upon interaction with an initiation energy; and (2) applying the initiation energy from an energy source to the medium or body, wherein the applied initiation energy interacts with the energy modulation agent to directly or indirectly produce the change in the medium or body by said emitted radiation, and wherein the energy modulation agent has a normal predominant emission of radiation in a first wavelength range (WR1) outside of a second wavelength range (WR2) known to produce the change, but under exposure to the applied initiation energy produces the change.

In a preferred embodiment of the present invention, the energy modulation agent can be a single energy modulation agent, or a combination or two or more energy modulation agents. The energy modulation agents of the present invention normally convert an incident radiation into a different energy by upconversion or downconversion. Each energy modulation agent typically has a predominant emission wavelength.

In a most preferred embodiment, the present invention methods apply an initiation energy to these energy modulation agents, which convert the initiation energy to an emitted radiation at a first wavelength range (WR1), which is indicative of the one or more energy modulation agents used. Interestingly, the present inventors have found that one can use these one or more energy modulation agents to initiate reactions, such as photoreactions, activating photo-activatable agents, curing photocurable media, etc, even when the reactions being initiated are not normally initiated by the first wavelength range (WR1), but are rather normally known to be activated by a second wavelength range (WR2) that is distinct and different from WR1. This is particularly surprising since the energy modulation agents used in this embodiment of the present invention are not known to emit radiation at any significant extent, intensity, spectral width, etc at the second wavelength range WR2 normally used to activate the reactions of interest.

While the inventors do not wish to be bound to any particular theory or proposed mechanism of action in such cases, it is speculated that the reactions are being activated by a previously unknown pathway, such as the synergistic combination of the emission spectra of the energy modulation agents to generate a wavelength of radiation not normally associated with either energy modulation agent being used, through some form of tunneling effect or photonic coupling (electronic or vibrational) effect to enhance or generate radiation at wavelengths not normally associated with either energy modulation agent, or a pathway not yet understood or known.

One possible mechanism involves the chemical interaction of combinations of phosphor materials in solution and/or under x-ray irradiation. Under x-ray exposure, some of the outer most atomic species of one phosphor might possibly leach into the media and diffuse through it to reach the surface(s) of another phosphor in the mixture. In effect, while the present invention is not limited to such an effect, phosphors in a given mixture may ion exchange. In one aspect of this phenomena, the gradient for ion exchange can be enhanced under x-ray exposure. It is known that some phosphors can form solid solutions. It is well known that solid solutions are formed between $Al_2O_3$ and $Cr_2O_3$ where one cation ($Al^{3+}$) in the host lattice can be substituted by another cation ($Cr^{3+}$). The size difference between Cr and Al are known to shift the emission of Ruby ($Al_2O_3$) from red to green.

The leaching of ionic species out and ion exchange between different phosphors would predominantly taking place at the outer most atomic layers with the exchange likely confined to the outer most atomic layers. For this reason, any new emissions (i.e., emissions which do not normally belong to either one of the original phosphors) would be expected to be weak by virtue of the lower number of newly formed emission sites that would be confined to the outer-most atomic layer (the outer surfaces of the particles). Indeed, observations of x-ray induced fluorescence from the combination of normally visibly emitting phosphors described below show the presence of comparatively weak emissions in the UV spectrum.

In one embodiment of this invention, the following "visible" phosphors can be used: $CaWO_4:Pb^{2+}$, $CaWO_4:W$, $Sr_3(PO_4)_2:Eu^{2+}$, $Ba_3(PO_4)_2:Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4:Mn^{2+}$, $Y_3(Al,Ga)_5O_{12}:Ce^{3+}$, $BaMg_2Al_{14}O_{24}:Mn^{2+}$, $BaMgAl_{14}O_{23}:Mn^{2+}$, $SrAl_{12}SiO_{19}:Mn^{2+}$, $ZnAl_{12}O_{19}:Mn^{2+}$, $CaAl_{12}O_{19}:Mn^{2+}$, $YBO_3:Tb^{3+}$, $Sr_4Si_3O_8Cl_4:Eu^{3+}$, $Y_2O_3:Eu^{3+}$, $Y_2SiO_5:Eu^{3+}$, $Y_3Al_5O_{12}:Eu^{3+}$, $CaSiO_3:Mn^{2+}$, $YVO_4:Eu^{3+}$, $Zn_2SiO_4:Mn^{2+}$, and combinations thereof.

Regardless of the exact mechanism, the invention provides methods for producing a change in a medium after generation of radiant energy inside the medium. In this method, an initiation energy source provides an initiation energy that penetrates the medium and induces a desired effect in the medium by way of interaction of the initiation energy with energy modulation agents (e.g., phosphors or combination of phosphors) which would not normally be expected to produce the desired effect (e.g., a UV-driven photoreaction).

In one embodiment, the effect produced occurs by photostimulation of a chemical reaction driven by a combination of emitters (e.g., x-ray downconverters or infrared upconverters) where the emitted light from each of the individual emitters is nominally not expected to drive the chemical reaction of interest (e.g., a UV-driven reaction stimulated primarily by light emitted in a visible spectrum or a UV-driven reaction stimulated by down-converting phosphors having respective emissions not in the UV range but driving the UV-driven reaction when combined.)

In one embodiment, the initiation energy source is applied directly or indirectly to the medium. Within the context of the invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the medium beneath the surface of the medium and to the activatable agents or energy modulation agents within a medium. In one embodiment, the initiation energy interacts with a previously supplied energy modulation agent which then activates the activatable agent.

Although not intending to be bound by any particular theory or be otherwise limited in any way, the following theoretical discussion of scientific principles and definitions are provided to help the reader gain an understanding and appreciation of the invention.

As used herein, an "activatable agent" is an agent that normally exists in an inactive state in the absence of an activation signal. When the agent is activated by an activation signal under activating conditions, the agent is capable of producing a desired pharmacological, cellular, chemical, electrical, or mechanical effect in a medium (i.e. a predetermined change). For example, when photocatalytic agents are irradiated with visible or UV light, these agents induce polymerization and "curing" of light sensitive adhesives.

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further require a set of activation conditions. For example, an activatable agent, such as a photosensitizer, may be activated by UV-A radiation (e.g., by UV-A radiation generated internally in the medium). For example, an activatable agent, such as a photosensitizer, may be activated by UV-B or UV-C radiation. Once activated, the agent in its active-state may then directly proceed to produce a predetermined change.

Where activation may further require other conditions, mere delivery of the activation signal may not be sufficient to bring about the predetermined change. For example, a photoactive compound that achieves its effect by binding to certain structure in its active state may require physical proximity to the target structure when the activation signal is delivered. For such activatable agents, delivery of the activation signal under non-activating conditions will not result in the desired effect. Some examples of activating conditions may include, but are not limited to, temperature, pH, location, state of the medium, and the presence or absence of co-factors or conformational changes.

Selection of an activatable agent greatly depends on a number of factors such as the desired change, the desired form of activation, as well as the physical and biochemical constraints that may apply. Exemplary activatable agents may include, but are not limited to agents that may be activated by photonic energy, electromagnetic energy, acoustic energy, chemical or enzymatic reactions, thermal energy, microwave energy, or any other suitable activation mechanisms.

When activated, the activatable agent may effect changes that include, but are not limited to an increase in organism activity, a fermentation, a decrease in organism activity, apoptosis, redirection of metabolic pathways, a sterilization of a medium, a cross polymerization and curing of a medium, or a cold pasteurization of a medium.

The mechanisms by which an activatable agent may achieve its desired effect are not particularly limited. Such mechanisms may include direct action on a predetermined target as well as indirect actions via alterations to the biochemical pathways. In one embodiment, the activatable agent is capable of chemically binding/associating to the organism in a medium. In this embodiment, the activatable agent, is exposed in situ to an activating energy emitted from an energy modulation agent, which, in turn receives energy from an initiation energy source.

Suitable activatable agents may be a small molecule, a biological molecule such as a protein, or cofactor, a nucleic acid or lipid; a supramolecular assembly; a nanoparticle; or any other molecular entity capable of producing a predetermined activity once activated.

The activatable agent may be derived from a natural or synthetic origin. Any such molecular entity that may be activated by a suitable activation signal source to effect a predetermined cellular change may be advantageously employed in the invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially interact/adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substitutes of the photosensitizers from which they are derived, and which preserve the function and substantial non-toxicity. Endogenous molecules are inherently non-toxic and may not yield toxic photoproducts after photoradiation.

FIG. 1 provides an exemplary electromagnetic spectrum in meters (1 nm equals 1 nanometer). As used herein, an "energy modulation agent" refers to an agent that is capable of receiving an energy input from a source and then re-emitting a different energy to a receiving target. Energy transfer among molecules may occur in a number of ways. The form of energy may be electronic, thermal, vibronic, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit energy in the form of thermal energy or energy which otherwise contributes to heating the environment in vicinity of the light emission.

Table 1 in FIG. 2 provides a list of photoactivatable agents that may be used as primary or secondary internal light sources. For example, the photoactivatable agents could be receptors of X-ray induced emissions from nanoparticles (to be discussed later) and which in turn emit a secondary light. In some mediums, it may be that the excitation wavelengths in Table 1 are transparent to the particular medium and the emission wavelengths are highly absorbent (due to, for example, molecular or solid state band gap transitions). In those cases, the photoreactive agents in Table 1 would be the primary sources for internal light generation.

In various embodiments, the energy modulation agent (down converters, mixtures of down converters, up converters, mixtures of up converters, and combinations thereof) receives energy (from a source and re-emits the energy (e.g. UV-A and/or visible light). Some energy modulation agents may have a very short energy retention time (on the order of femtoseconds (fs), e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a quantum dot, a quantum dot encapsulated by polyamidoamine dendrimers, a luciferase, a biocompatible phosphorescent molecule, a combined electromagnetic energy harvester molecule, and a lanthanide chelate capable of intense luminescence. These energy modulation agents (some of which are described above as nanoparticles) need not be of nanometer size and can in various embodiments of this invention be of micron-sized proportions. Typically, the energy modulation agents (down converters, mixtures of down converters, up converters, mixtures of up converters, and combinations thereof) induce photoreactive changes in the medium and are not used for the purpose of exclusively heating the medium.

Various exemplary uses are described in the embodiments below.

The energy modulation agents may further be coupled to a carrier for targeting purposes. For example, a biocompatible molecule, such as a fluorescing metal nanoparticle or fluorescing dye molecule that emits in the UV-A band, may be selected as the energy modulation agent. The energy modulation agent may be preferably directed to the desired site by systemic administration into a medium. For example, a UV-A emitting energy modulation agent may be distributed in the medium by physical insertion and or mixing, or by conjugating the UV-A emitting energy modulation agent with a specific carrier, such as a protein or peptide, lipid, chitin or chitin-derivative, a chelate or other functionalized carrier that is capable of concentrating the UV-A emitting source in a specific target region of the medium.

Additionally, the energy modulation agent can be used alone or as a series of two or more energy modulation agents such that the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable agent. Alternatively, one or more energy modulation agents in the cascade may also activate additional activatable agents.

Although the activatable agent and the energy modulation agent can be distinct and separate, it will be understood that the two agents need not be independent and separate entities. In fact, the two agents may be associated with each other via a number of different configurations. Where the two agents are independent and separately movable from each other, they can generally interact with each other via diffusion, ion-exchange, electrostatic attraction and chance encounters within a common surrounding medium. Where the activatable agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include any device capable of generating x-ray, y-ray, gamma-ray, or electron beams.

In one embodiment, the initiation energy is capable of penetrating completely through the medium. Within the context of the invention, the phrase "capable of penetrating completely through the medium" is used to refer to energy capable of penetrating a container to any distance necessary to activate the activatable agent within the medium. It is not required that the energy applied actually pass completely through the medium, merely that it be capable of doing so in order to permit penetration to any desired distance to activate the activatable agent. The type of energy source chosen will depend on the medium itself.

Photoactivatable agents may be stimulated by an energy source through mechanisms such as irradiation, resonance energy transfer, exciton migration, ion-exchange, free radicals, electron injection, or chemical reaction, to an activated energy state that is capable of producing the predetermined change desired. One advantage is that wavelengths of emitted radiation may be used to selectively stimulate one or more photoactivatable agents or energy modulation agents capable of stimulating the one or more photoactivatable agents. The energy modulation agent is suitably stimulated at a wavelength and energy that causes little or no change to the medium.

Within the context of the invention, the applying of the initiation energy source means the application of an agent, that itself produces the initiation energy, in a manner that permits the agent to arrive at the target structure within the medium. The application can take any form. Further, the initiation energy source in this embodiment can be in any form, including, but not limited to, tablet, powder, liquid solution, liquid suspension, liquid dispersion, gas or vapor, etc.

In another embodiment, the invention includes the application of the activatable agent, along with a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the medium or inside the medium, with the chemiluminescence, phosphorescence or bioluminescence being allowed to activate the activatable agent in the medium. The administration of the activatable agent and the source of chemical energy can be performed sequentially in any order or can be performed simultaneously.

In the case of certain sources of such chemical energy, the application of the chemical energy source can be performed after activation outside the medium, with the lifetime of the emission of the energy being up to several hours for certain types of phosphorescent materials for example.

When molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media, the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity.

The molecule subsequently deactivates to the lowest vibronic levels of $S_{n-1}$ via a VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local changes in the medium.

Light absorbing species in various embodiments can include natural chromophores in tissue or exogenous dye compounds such as indocyanine green, naphthalocyanines, and porphyrins coordinated with transition metals and metallic nanoparticles and nanoshells of metals.

Yet another example is that nanoparticles or nanoclusters of certain atoms may be introduced such that they are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a medium are capable of stimulating activation of photoactivatable agents disposed in a distant portion of the medium, so long as the distance does not greatly exceed $R_0$. For example, gold nanospheres having a size of 5 atoms of gold have been shown to have an emission band in the ultraviolet range, recently.

In an additional embodiment, the photoactivatable agent can be a photocaged complex having an active agent (which can be an activatable agent) contained within a photocage. In various embodiments, the photocage molecule releases the agent into the medium. The active agent can be bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths.

In one embodiment of this invention, medical bottle caps which need to be sterilized have under the base cap material a glued seal material which contacts the base of the medical bottle. Because steam autoclaves are insufficient for this purpose, one embodiment of the invention uses luminescing particles included in the adhesive layer when the seal material is applied to the bottle cap. Then, X-ray irradiation becomes capable of curing the adhesive and producing within the adhesive medium radiation for direct sterilization or the production of singlet oxygen and/or ozone for biological germicide.

The activatable agent and derivatives thereof as well as the energy modulation agent, can be incorporated into compositions suitable for delivery to particular mediums. The composition can also include at least one additive having a complementary effect upon the medium, such as a lubricant or a sealant.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Referring to FIG. 3A, an exemplary system according to one embodiment of the invention may have an initiation energy source 1 directed at medium 4. Activatable agents 2 and an energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 3 as silica encased energy modulation agents. As shown in FIG. 3A, initiation energy 7 in the form of radiation from the initiation energy source 1 permeated throughout the medium 4. The initiation energy source 1 can be an external energy source or an energy source located at least partially in the medium 4. Activatable agents 2 and/or the energy modulation agents 3 can include plasmonics agents which enhance either the applied energy or the energy emitted from the energy modulation agents 3 so as to directly or indirectly produce a change in the medium.

In various embodiments, the initiation energy source 1 may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

According to another embodiment of the invention, energy modulation elements 6 can be placed in the vicinity of a fluid medium 4 (e.g., a liquid or other fluid-like medium) and held inside a container. The container can be made of a material that is "transparent" to the radiation. For example, plastic, quartz, glass, or aluminum containers would be sufficiently transparent to X-rays, while plastic or quartz or glass containers would be transparent to microwave or radio frequency light. The energy modulation elements 6 can be dispersed uniformly throughout the medium or may be segregated in distinct parts of the medium or further separated physically from the medium by encapsulation structures. A supply would provide the medium 4 to the container.

Figure 3B:
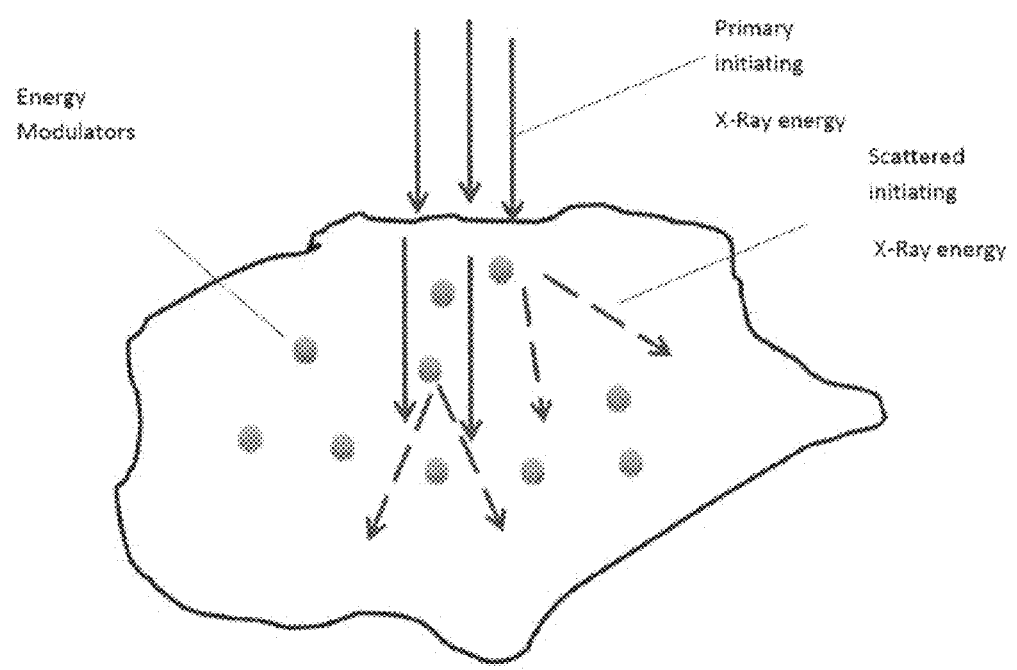
FIG. 3B is a schematic depicting x-ray scattering events and interactions with energy modulation agents in the medium.

FIG. 3B is a schematic depicting x-ray scattering events and interactions with energy modulation agents in the medium. In one embodiment, the effect produced by the interactions of the x-rays and energy modulation agents with the medium occurs by pathways not yet certain where internally produced light (IR, visible, and/or UV) alone or in combination with the x-ray exposure drive a chemical reaction in the medium or to the energy modulation agents themselves. These pathways may be influenced by the generation of free radicals inside the medium. These pathways may be influenced by the generation of ions inside the medium. These pathways may be influenced by the scattering of x-rays inside the medium. These pathways may be influenced by the generation of emitted and re-emitted light in inside the medium. These pathways may be a combination of these factors.

Further, these pathways may include the in situ generation of singlet oxygen and/or ozone to produce a change in the medium. For example, the photoactivatable agents may be stimulated through mechanisms such as irradiation, resonance energy transfer, exciton migration, ion-exchange, free radicals, electron injection, or chemical reaction to where "activated" agent is capable of producing the predetermined change desired.

In another embodiment, clusters of energy modulations agents (or chemically reactive agents or plasmonic agents) may be provided to a local site where x-ray exposure or internally generated light breaks apart the clusters into a form more useful to treatment at the local site or more useful to generating a local change in the medium nearby where the clusters existed.

Figure 3C:
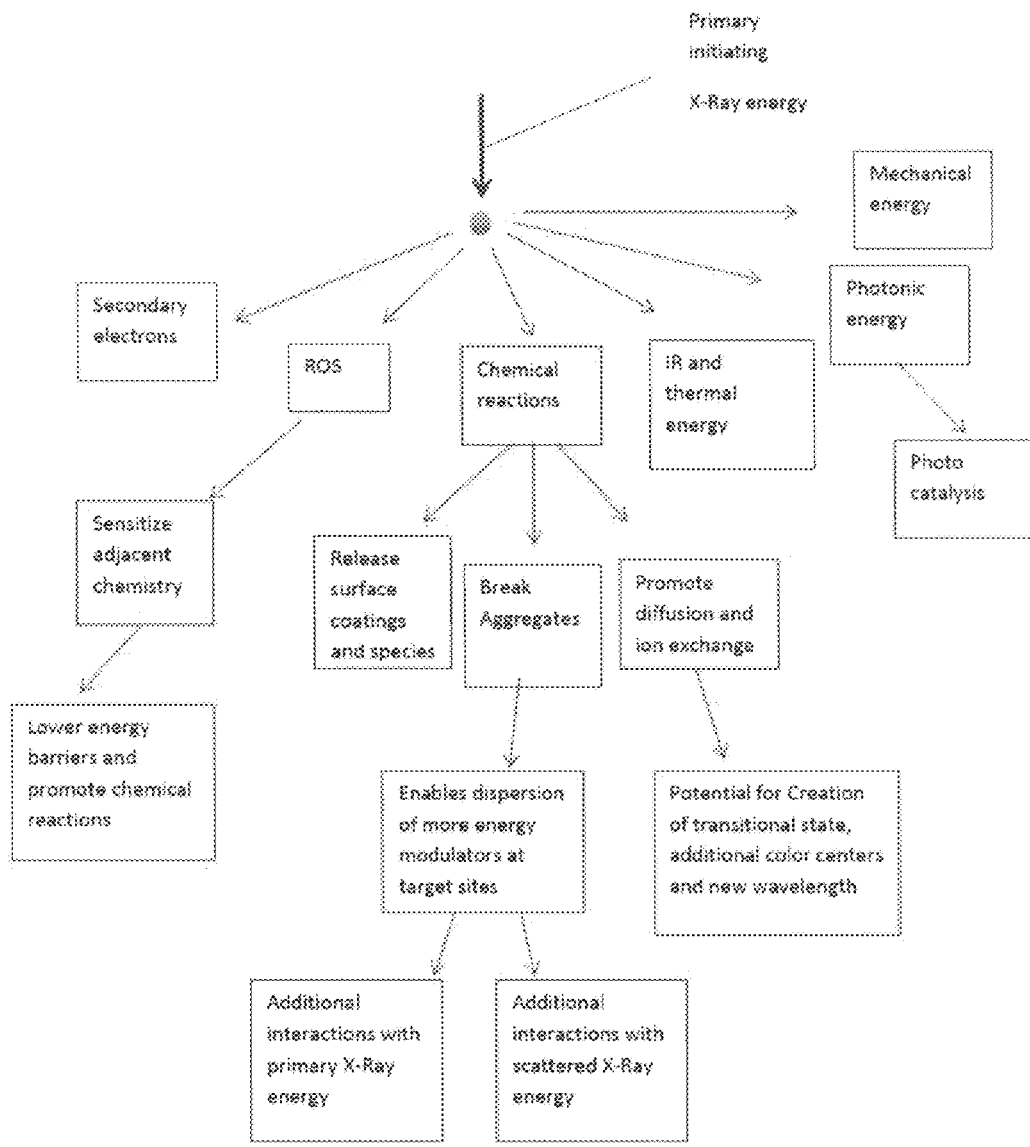
FIG. 3C is a depiction of a cascade of reactions whereby the initiation energy interacts with the energy modulation agents and other constituents in the medium.

FIG. 3C is a depiction of a cascade of reactions whereby the initiation energy interacts with the energy modulation agents and other constituents in the medium to produce a number of primary and secondary reactions. These interactions for example can lead to the production of electrons and/or reactive oxygen species (ROS), can sensitize adjacent chemistry, lower energy barriers and promote chemical reactions, can drive chemical reactions, release surface coatings and species, and/or break aggregates permitting the dispersion of more energy modulators at target sites, can promote additional interactions with primary X-Ray energy, promote additional interactions with scattered X-Ray energy, and/or promote diffusion and ion exchange, can provide a potential for creation of a transitional state and/or provide additional color centers, and can be responsible for emissions at new wavelengths of UV, visible, infrared, or thermal energy not normally present without these interactions. These interactions can result in increased photonic energy, can drive photo catalysis, and can provide mechanical energy to the medium.

As an illustration of a complex interaction process of this invention, in one embodiment, a coating is applied to an energy modulator. The coating has at least one embedded (not tethered) biotherapeutic agent. The coating is made of chemicals that maintain emissions from the energy modulator (e.g., known visible or UV emissions). The coated energy modulator is delivered to the medium and exposed to x-rays with an intensity that allows the breaking of the coating or the breaking of the outer surfaces of the phosphors (which then releases the biotherapeutic agent). Optionally, the x-ray energy and/or intensity can be lowered to activate photonic emission of the phosphor without necessarily further surface aberration.

In the invention, energy transfer among molecules may occur in a number of ways. The form of energy may be electronic, thermal, electromagnetic, kinetic, or chemical in nature. The energy can be modulated up to emit higher energy from the energy modulation agent compared to the input initiation energy, or can be modulated down to emit lower energy from the energy modulation agent compared to the input initiation energy. Energy may be transferred from one molecule to another (intermolecular transfer) or from one part of a molecule to another part of the same molecule (intramolecular transfer). For example, a modulation agent may receive electromagnetic energy and re-emit the energy in the form of a different energy. In various embodiments, the energy modulation agents receive higher energy (e.g. x-ray) and re-emits in lower energy (e.g. UV-A, UV-B, UV-C). In other embodiments, different energy modulation agents would receive lower energy (e.g., infrared or near-infrared) and emits in a higher energy (e.g., visible or ultraviolet).

Energy transfer processes are also referred to as molecular excitation. Some modulation agents may have a very short energy retention time (on the order of fs-ns, e.g. fluorescent molecules) whereas others may have a very long half-life (on the order of seconds to hours, e.g. luminescent inorganic molecules or phosphorescent molecules). Suitable energy modulation agents include, but are not limited to, a metal nanoparticle or a biocompatible metal nanoparticle, a metal coated or uncoated with a biocompatible outer layer, a chemiluminescent molecule whose rate of luminescence is increased by microwave activation, fluorescing dye molecule, gold nanoparticle, a water soluble quantum dot encapsulated by polyamidoamine dendrimers, a luciferase, a biocompatible phosphorescent molecule, a biocompatible fluorescent molecule, a biocompatible scattering molecule, a combined electromagnetic energy harvester molecule, and a lanthanide chelate capable of intense luminescence. As noted above, these energy modulation agents (some of which are described above as nanoparticles) need not be of nanometer size and can in various embodiments of this invention be of micron-sized proportions. Various exemplary uses of the energy modulation agents of this invention are described.

The modulation agents may further be coupled to a carrier for targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. in close vicinity to a photoactive substance such as for example a photocatalyst or a photo initiator) by pre-distribution of the energy modulation agent into a medium to be exposed to the activation energy. For example, a UV-A emitting energy modulation agent may be concentrated in joints for adhesion of two parts together by physical insertion or by conjugating the UV-A emitting energy modulation agent with a photoactivatable resin.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the photo-activatable agent in the medium.

Although the photo-activatable agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion, electrostatic interactions and chance encounters within a common surrounding medium. Where the photo-activatable agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, UV-A lamps, UV-B lamps, UC-C lamps, or fiber optic lines, a light needle, an endoscope, and a linear accelerator that generates x-ray, gamma-ray, or electron beams. The energy used can be any type, including but not limited to, gamma ray, x-ray, UV, near-UV, visible, Near IR, IR, microwave, radio wave, etc. In a preferred embodiment, the initiation energy capable of penetrating completely through the subject. Exemplary initiation energy sources that are capable of penetrating completely through the subject include, but are not limited to, x-rays, gamma rays, electron beams, microwaves and radio waves.

In one embodiment of this invention, plasmonic structures can be utilized. The plasmonics-enhanced principle is based in theory on enhancement mechanisms of the electromagnetic field effect. Electromagnetic enhancements are divided into two main classes: a) enhancements that occur only in the presence of a radiation field, and b) enhancements that occur even without a radiation field. The first class of enhancements is further divided into several processes. Plasma resonances on substrate surfaces, also called surface plasmons, provide a significant contribution to electromagnetic enhancement. One effective type of plasmonics-active substrate includes nanostructured metal particles, protrusions, or rough surfaces of metallic materials. Incident light irradiating these surfaces excites conduction electrons in the metal, and induces the excitation of surface plasmons leading to Raman/luminescence enhancement. At a plasmon frequency, metal nanoparticles (or other nanostructured roughened structures) become polarized, resulting in large field-induced polarizations and thus large local fields on the surface. These local fields increase the luminescence/Raman emission intensity, which is proportional to the square of the applied field at the molecule.

As a result, the effective electromagnetic field experienced by an analyte molecule on these surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

Accordingly, plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient strategy for the efficient use of internally generated light.

Accordingly, the invention utilizes several important mechanisms:
  (A) Increased absorption of the excitation light by the plasmonic metal nanoparticles, resulting in enhanced photoactivation of photoinitiators or photocatalysts;
  (B) Increased absorption of the excitation light by the plasmonic metal nanoparticles that serve as more efficient energy modulation agent systems, yielding more light for increased excitation of the photoinitiators or photocatalysts;
  (C) Increased absorption of the excitation light by the medium material on or near the plasmonic metal nanoparticles;
  (D) Increased light absorption of the energy modulation agent molecules adsorbed on or near the metal nanoparticles;
  (E) Amplified light emission from the energy modulation agent molecules adsorbed on or near the metal nanoparticles; and
  (F) Increased absorption of emission light emitted from the energy modulation agent by the photoinitiators or photocatalysts.

Figure 5A:
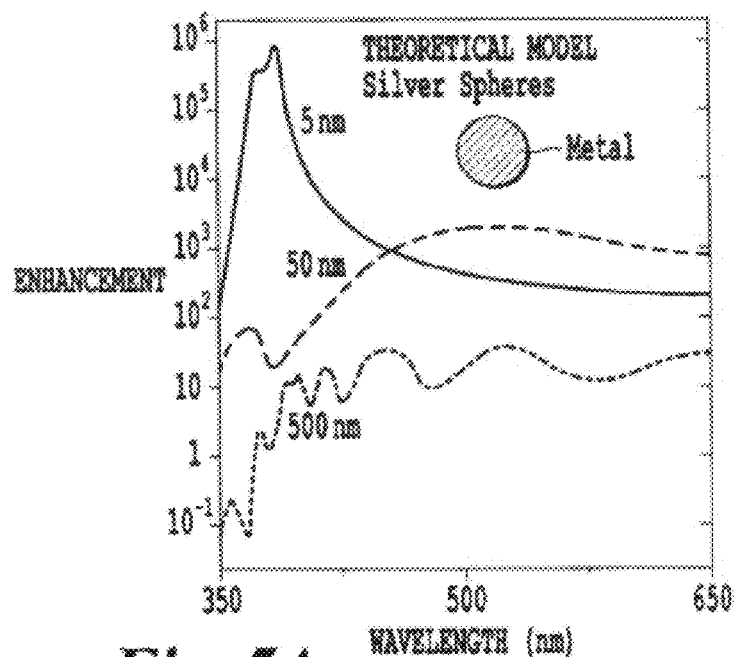
FIGS. 5A and 5B are representations of plasmonic nanostructures and their theoretical electromagnetic enhancement at different excitation wavelength.
Figure 5B:
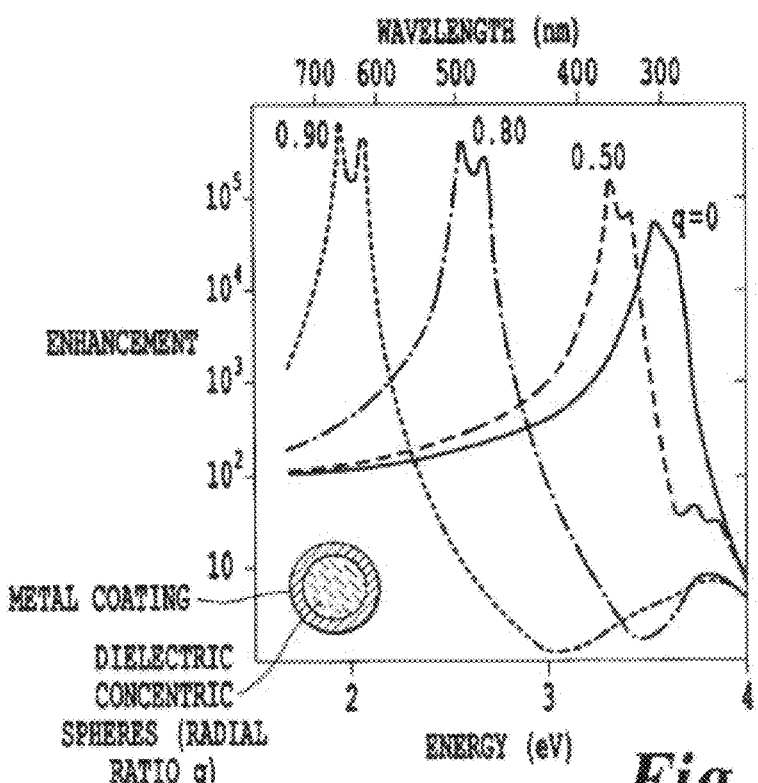

As discussed above, one of several phenomena that can enhance the efficiency of light emitted (Raman or luminescence) from molecules adsorbed or near a metal nanostructures Raman scatter is the surface-enhanced Raman scattering (SERS) effect. In 1984, the general applicability of SERS as an analytical technique was first reported by one of the present inventors, and the possibility of SERS measurement for a variety of chemicals including several homocyclic and heterocyclic polyaromatic compounds [T. Vo-Dinh, M. Y. K. Hiromoto, G. M. Begun and R. L. Moody, "*Surface-enhanced Raman spectroscopy for trace organic analysis,*" *Anal. Chem.*, vol. 56, 1667, 1984], the entire contents of which are incorporated herein by reference. Extensive research has been devoted to understanding and modeling the Raman enhancement in SERS since the mid 1980's. FIG. 5, for example, shows the early work by Kerker modeling electromagnetic field enhancements for spherical silver nanoparticles and metallic nanoshells around dielectric cores as far back as 1984 [M. M. Kerker, *Acc. Chem. Res.*, 17, 370 (1984)], the entire contents of which are incorporated herein by reference. This figure shows the result of theoretical calculations of electromagnetic enhancements for isolated spherical nanospheres and nanoshells at different excitation wavelengths. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

Theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons," and b) an effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

FIGS. 6A-6G shows a number of the various embodiments of plasmonics-enhanced probe structures (PEPST) that can be designed:
 (A) Photo-activatable (PA) molecules bound to a metal (e.g., gold) nanoparticle;
 (B) Photo-activatable (PA) molecule covered with metal nanoparticles;
 (C) Metal nanoparticle covered with PA nanocap;
 (D) PA-containing nanoparticle covered with metal nanocap;
 (E) Metal nanoparticle covered with PA nanoshell;
 (F) PA-containing nanoparticle covered with metal nanoshell; and
 (G) PA-containing nanoparticle covered with metal nanoshell with protective coating layer.

Figure 7A:
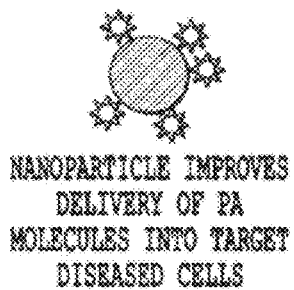
Figure 9:
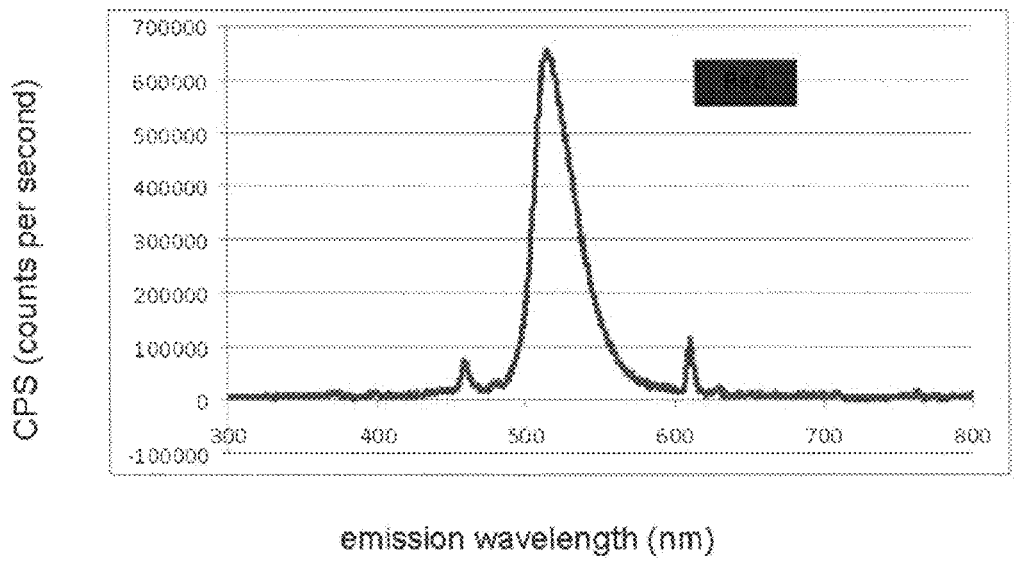
FIG. 9 is a depiction of an x-ray induced optical emission spectra from a red (R) phosphor.
Figure 10:
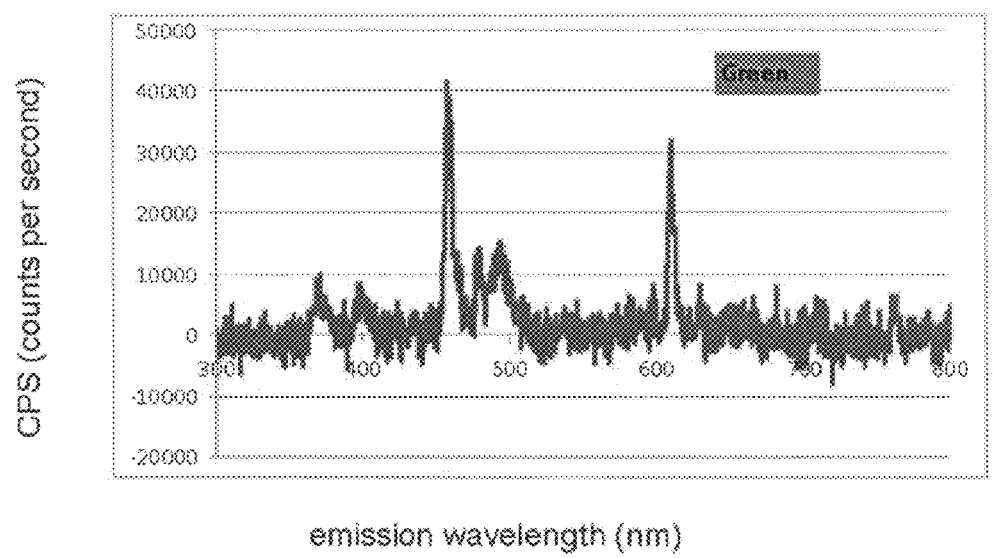
FIG. 10 is a depiction of an x-ray induced optical emission spectra from a green (G) phosphor.
Figure 11:
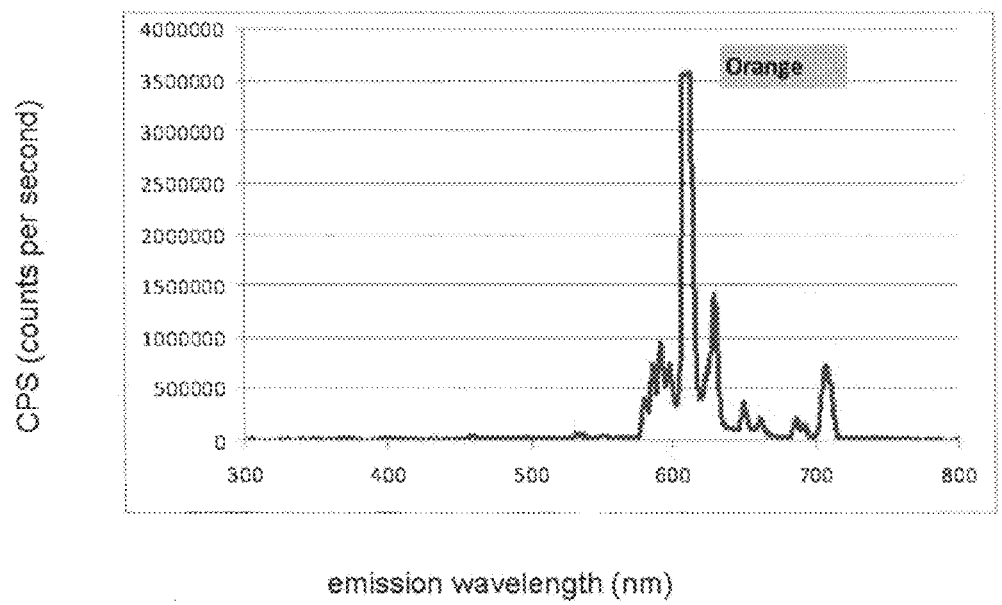
FIG. 11 is a depiction of an x-ray induced optical emission spectra from an orange (O) phosphor.
Figure 12:
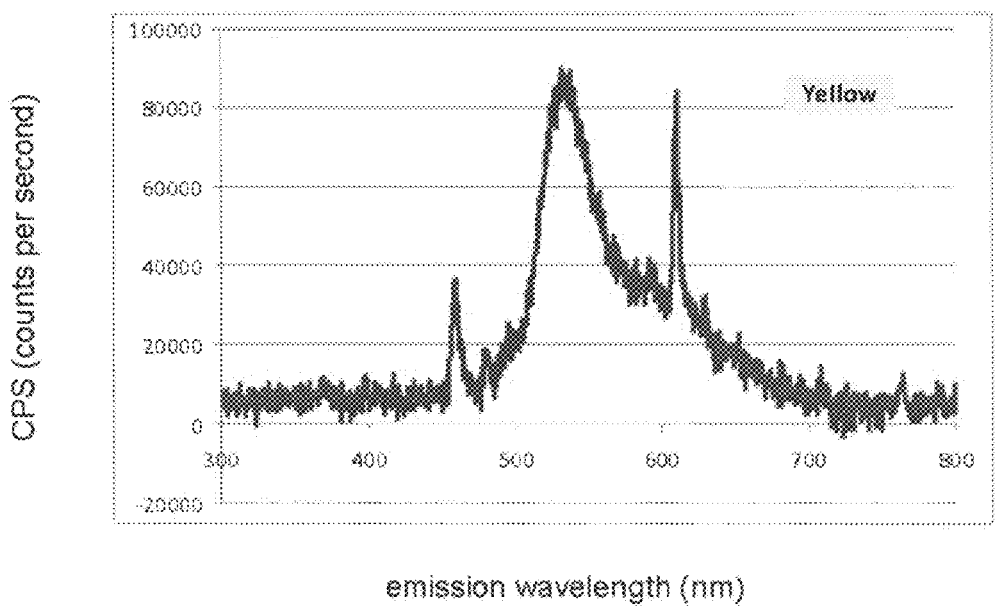
FIG. 12 is a depiction of an x-ray induced optical emission spectra from a yellow (Y) phosphor.

A basic embodiment is shown in FIG. 6A. This embodiment shows a PA molecules bound to a metal (e.g., gold) nanoparticle. FIG. 7 illustrates the plasmonics-enhancement effect as it would be used in this invention to enhance the interaction of the primary excitation light source with energy modulation agents or to enhance the interaction of the secondarily produced light with the medium in effecting a change to the medium. Radiation of suitable energy is used to excite the plasmonic structures which in turn activates for example nearby photoinitiators.

For example, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in an increased photoactivation of a photo-initiator or a photo-catalyst and improved reaction kinetic. Further, for sterilization applications, the effect increases the likelihood for a germicide event in the medium in vicinity of the nanoparticles. While light such as the HeNe laser light might be scattered and absorbed in the medium, the presence of the PEPST structures enhances the interaction of the penetrating light beyond that which would normally be considered useful. The plasmonics-enhanced mechanism can also be used with the other PEPST probes in FIGS. 6B, 6C, 6D, 6E, 6F and 6G.

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy, and new photonic devices.

In one embodiment of the invention, the plasmonic structures have a metallic layer over a dielectric core. In one embodiment of the invention, these shells include spheroidal shells, since the plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. The invention also includes prolate and oblate spheroidal shells, which show some interesting qualitative features in their plasmon resonances. The spheroidal shell presents two degrees of freedom for tuning: the shell thickness and the shell aspect ratio [S. J. Norton and T. Vo-Dinh, "*Plasmonic Resonances of Nanoshells of Spheroidal Shape*", *IEEE Trans. Nanotechnology*, 6, 627-638 (2007)] the entire contents of which are incorporated herein by reference.

FIG. 7 shows some of the various embodiments of plasmonics-active nanostructures that can be designed, and are preferred embodiments of this invention:
 (A) Metal nanoparticle;
 (B) Dielectric nanoparticle core covered with metal nanocap;
 (C) Spherical metal nanoshell covering dielectric spheroid core;
 (D) Oblate metal nanoshell covering dielectric spheroid core;
 (E) Metal nanoparticle core covered with dielectric nanoshell;
 (F) Metal nanoshell with protective coating layer;

(G) Multi layer metal nanoshells covering dielectric spheroid core;

(H) Multi-nanoparticle structures;

(I) Metal nanocube and nanotriangle/nanoprism; and (J) Metal cylinder.

In a further embodiment of the invention, the PA molecules can be incorporated into a material (e.g., biocompatible polymer) that can form a nanocap onto the metal (gold) nanoparticles. The material can be a gel or biocompatible polymer that can have long-term continuous release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers.

FIG. 8 shows other possible plasmonic embodiments of this invention with dielectric down-converting or up-converting material materials in proximity to metal shells or coatings. A plasmonics enhanced effect can occur throughout the electromagnetic region provided suitable nanostructures, nanoscale dimensions, metal types are used.

In various embodiments of this invention, the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

The energy modulation agent materials can include any materials that can absorb X ray and emit light in order to excite the PA molecule. The energy modulation agent materials include, but are not limited to:

metals (gold, silver, etc);

quantum dots;

semiconductor materials;

scintillation and phosphor materials;

materials that exhibit X-ray excited luminescence (XEOL);

organic solids, metal complexes, inorganic solids, crystals, rare earth materials (lanthanides), polymers, scintillators, phosphor materials, etc.; and materials that exhibit excitonic properties.

Quantum dots, semiconductor nanostructures and various materials related to quantum dots, semiconductor materials, etc. can be used as energy modulation agents. Scintillator materials can be used as energy modulation agents. Various scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al, *Nuclear Instrum. Meth. In Physics Res*. A, 486, 295 (2002, the entire contents of which are incorporated herein by reference]. For example CdS (or CsCl) exhibit luminescence when excited by soft X-ray [Jaegle et al, *J. Appl. Phys.*, 81, 2406, 1997, the entire contents of which are incorporated herein by reference]. XEOL materials such as lanthanides or rare earth materials can be used as energy modulation agents.

In the invention, the experimental parameters including size, shape and metal type of the nano structure can be selected based upon the excitation radiation, the photoactivation radiation, and/or the emission process from the energy modulation agent system.

Combination Emitter Stimulation

As noted above, the invention provides methods for producing a change in a medium or body after generation of radiation inside the medium. In this method, an initiation energy source provides an initiation energy that penetrates the medium and induces internal radiation to produce a desired effect in the medium. In one embodiment of this invention, the effect produced occurs by photo stimulation of a chemical reaction driven by a combination of emitters (e.g., x-ray down-converters) where the emitted light from each of the emitters individually is nominally not expected to drive the chemical reaction (e.g., a UV-driven reaction stimulated primarily by light emitted in a visible spectrum or a UV-driven reaction stimulated by down-converting phosphors having respective emissions not in the UV range but may exhibit UV emission when combined.)

In a most preferred embodiment, the present inventors have found that chemical reactions known in the art to be driven by UV radiation in the 300 to 400 nm range can be stimulated from light emitted from energy converters which are considered to nominally have no emission in the 300 to 400 nm range. The exact mechanism of this stimulation is not known at this time. There is optical data evidence showing that the combination of visible emitters produces an emission in the UV range. In other words, the inventors have discovered that combination of visible emitters yields more than the expected summation of the emission peaks. In some cases, new peaks are observed in the UV range. In other cases, prominent peaks in the visible range disappear.

The data in the following figures show this effect.

FIGS. 9-12 show respective x-ray induced optical emission spectra from phosphors having their dominant emissions in the red, green, orange, and yellow parts of the visible spectrum, respectively. The phosphors were obtained from the following sources. "Ruby Red" obtained from Voltarc, Masonlite & Kulka, Orange, Conn., and referred to as "Neo Ruby"; "Flamingo Red" obtained from EGL Lighting, Berkeley Heights, N.J. and referred to as "Flamingo"; "Green" obtained from EGL Lighting, Berkeley Heights, N.J. and referred to as "Tropic Green"; "Orange" obtained from Voltarc, Masonlite & Kulka, Orange, Conn., and referred to as "Majestic Orange"; "Yellow" obtained from Voltarc, Masonlite & Kulka, Orange, Conn., and referred to as "Clear Bright Yellow." The "BP" phosphors are shown in detail below:

| Code | Phosphor Material Color | Emission Spectrum Peak Emission (nm) | X-Ray Absorption Emiss Eff (%) | Eff (Z) | K-edge (keV) | Denisty g/cc Specific Gravity | Xtal Crystal Structure | Hygroscopic |
|---|---|---|---|---|---|---|---|---|
| BP1 | CaWO4: Pb | 425 | | | | | | N |
| BP2 | Y2SiOS: Ce | 410 | | | | | | N |
| BP3 | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF - 1 | 460 | | | | | | |
| BP5 | BASF-2 | 490 | | | | | | |
| BP6 | YTaO4: Nb (*) | 410 | 11 | 59.8 | 67.42 | 7.5 | Monolithic | N |
| BP6-C | YTaO4: Nb (*) | | | | | | | |
| BP7-C | LaOBr: Tm3+ (coated) | 360, 460 | 14 | 49.3 | 38.92 | 6.3 | Tetragonal | N |
| BP8-C | Laf3: Ce | 280 | | | | | | |
| BP9 | Y2O3 | 365 | | | | | | |
| BP-10 | BaSO4—: Eu2+ (coated) | 390 | 6 | 45.5 | 37.38 | 4.5 | Rhombic | N |
| BP10-C | BaSO4—: Eu2+ (coated) | 390 | 6 | 45.5 | 37.38 | 4.5 | Rhombic | N |
| BP11 | LaOCl: Tm | | | | | | | |
| BP12 | Y2O2S: Tm | | | | | | | |
| BP13 | BaSi2O5: Pb2+ | 350 | | | | | | N |
| | SrB6O10: Pb | 360 | | | | | | N |
| | CsI: Na (Coated) | 338 | | | | | | Y |
| | Gd2O2S: Tm | Blue to Green | | | | | | Y |

The "BP" phosphors are available from PhosphorTech Corporation of Kennesaw, Ga. and from BASF Corporation.

In general, these phosphors show individually the emission of radiation at wavelengths other than the "primary" color. While these phosphors show little if any indication of emission in the 300 to 400 nm range, the results below show the "UV-activity" of these phosphors once x-ray activated.

When a "photo-caged" luciferin is exposed to UV light in the 300 to 400 nm range, its photocage breaks releasing d-luciferin. Since d-luciferin emits visible light upon reaction with luciferase and appropriate co-factors, exposure of the released d-luciferin to a controlled amount of luciferase provides for visible light production where the amount of visible light produced will be indicative of the amount of d-luciferin uncaged, and evidence of UV activation.

Figure 13:
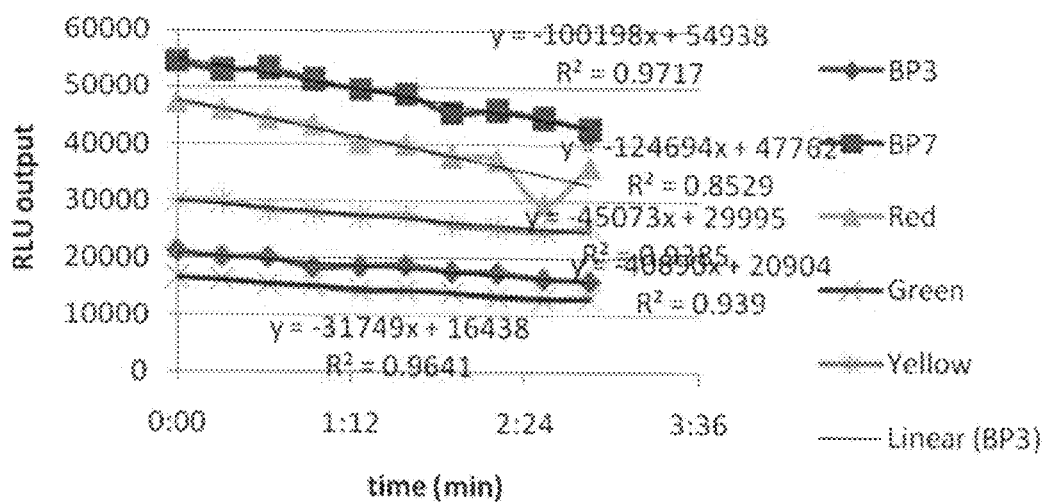
FIG. 13 is a plot of the levels of relative light output for d-luciferin/luciferase reactions obtained over time for individual types of phosphors (i.e., no mixtures) exciting a UV-light severable photocage containing d-luciferin.

FIG. 13 is a plot of the levels of relative light output for d-luciferin/luciferase reactions obtained over time for individual types of phosphors (i.e., no mixtures) exciting a UV-light severable photocage containing d-luciferin. The data shows that some light is output which may be due to nucleophilic hydrolysis (i.e. hydroxide ion mediated) of the photocage by the phosphor additions. The plot shows that the level of light output peaks initially and then decays over time.

Figure 14:
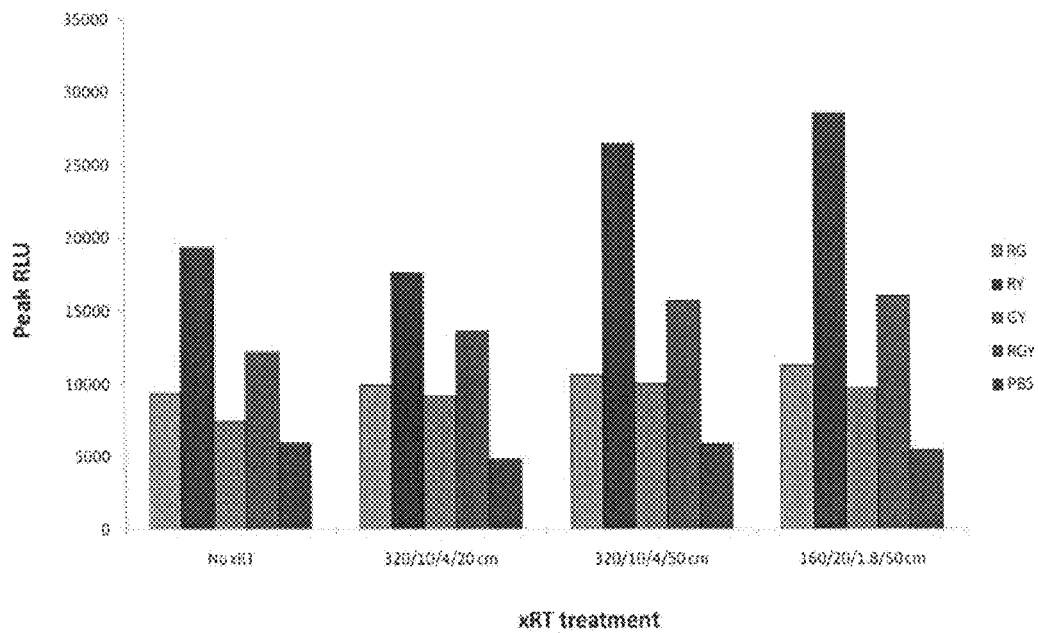
FIG. 14 is a chart comparing peak levels of light output for the for d-luciferin/luciferase reactions from different mixtures (red-green RG, red-yellow RY, green-yellow GY, red-green-yellow RGY exposed to x-ray radiation)

FIG. 14 is a chart comparing peak levels of read-out light from different mixtures (red-green RG, red-yellow RY, green-yellow GY, red-green-yellow RGY). The first data group to the left-most set shows a control with the phosphor combinations not being exposed to x-ray. PBS represents a phosphate buffered saline control for each of the sets. The second data group to the right shows little change in the read-out levels for the x-ray kVp energy/phosphor loading (milligrams)/x-ray time/x-ray source distance (cm) of 320/10/4/20. However, the third data group to the right and the fourth data group to the right show significant light out put when either the x-ray source distance increased or the phosphor loading increased). Of these phosphor combinations, the red yellow RY phosphor combination showed the highest increase.

Figure 15:
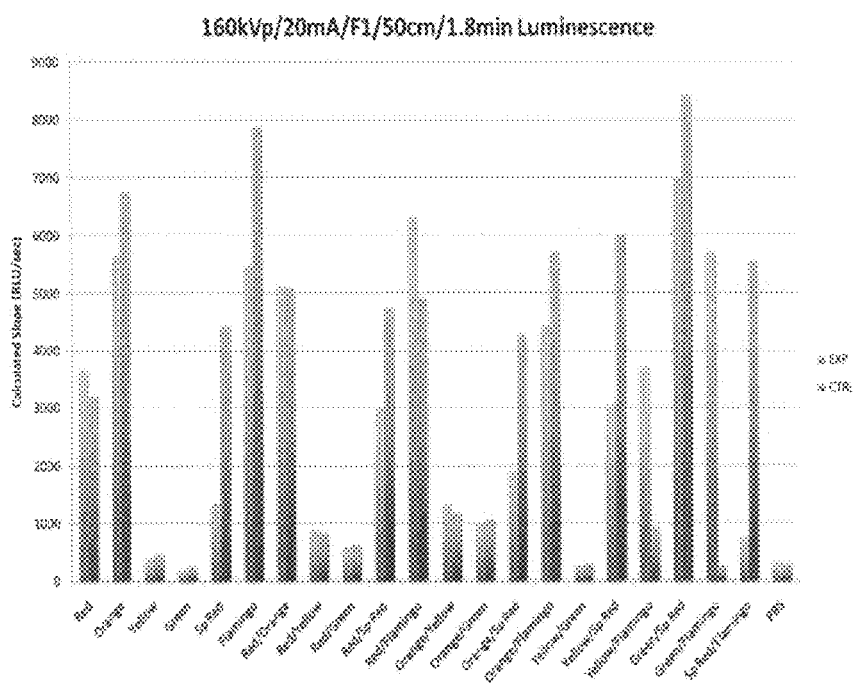
FIG. 15 is plot of a number of different phosphor combinations tested at 160 kVp/20 mA anode current/an aluminum filter in the x-ray beam/50 cm spacing conditions for a 1.8 minute x-ray exposure, except of the phosphor group with no exposure to x-ray radiation (the control set)

FIG. 15 is plot of a number of different phosphor combinations tested at 160 kVp/20 mA anode current/an aluminum filter in the x-ray beam/50 cm spacing conditions for a 1.8 minute x-ray exposure, except of the phosphor group with no exposure to x-ray radiation (the control set marked "CTRL"). FIG. 15 shows that phosphor combinations which showed the highest light output relative to the control were red-flamingo (RF) and green-flamingo (GF). Red-yellow (RY) and orange-yellow (OY) also showed higher light outputs relative to the control.

Figure 16:
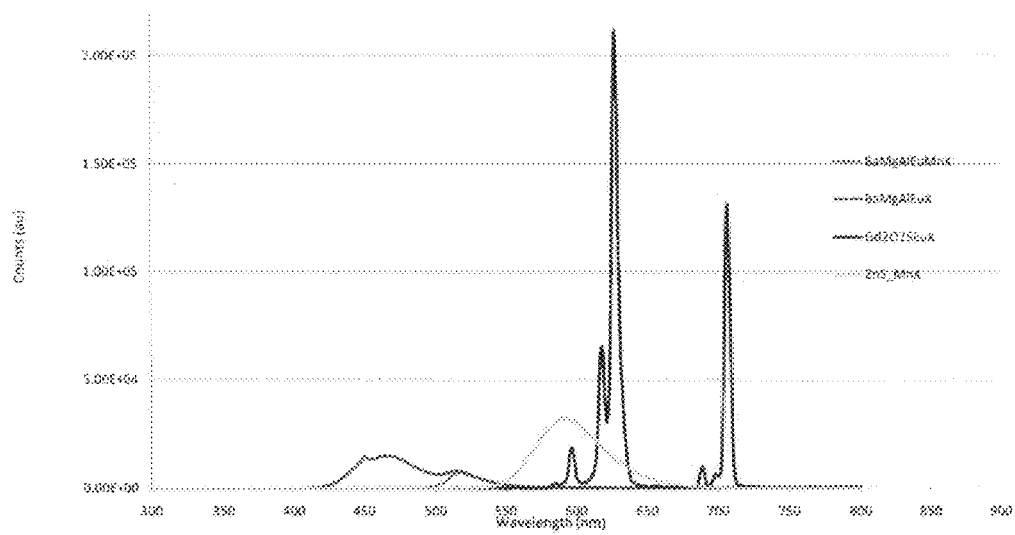
FIG. 16 is a composite of x-ray induced optical emission spectra of various individual visible emitting phosphors overlaid on each other.

FIG. 16 is a composite plot of x-ray induced optical emission spectra of various individual visible emitting phosphors overlaid on each other. The "$Gd_2O_2SEuX$" phosphor is the strongest emitter. The "BaMgAlEuX" phosphor has peaks the closest to the UV range. (The "X" here refers to a dopant element present such as for example Tm.)

Yet, when combinations of these phosphors are used as x-ray induced down conversion to drive reactions known to be driven by UV wavelengths in the 300 to 400 nm range, unexpectedly, photoreactions occur.

Figure 17A:
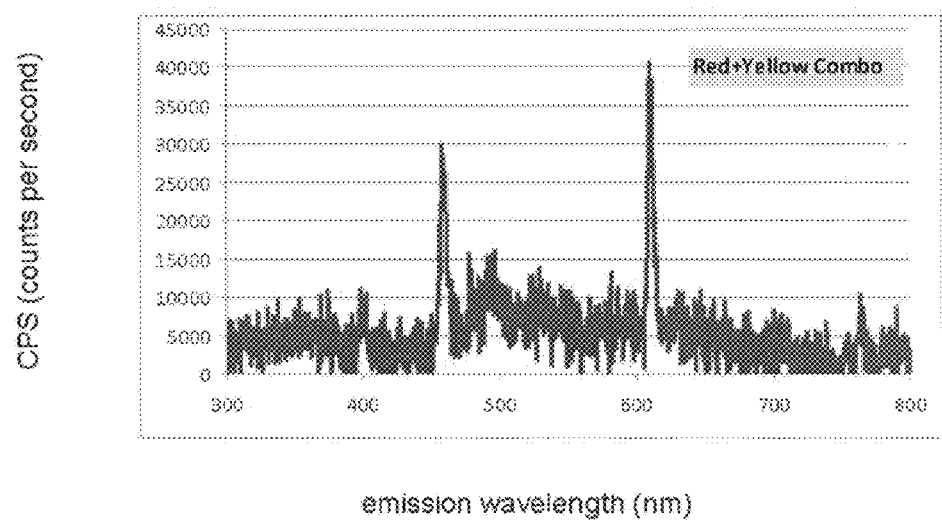
FIG. 17A is a depiction of an x-ray induced optical emission spectrum from a red-yellow RY phosphor combination.

Optically, certain combinations of these phosphors showed more than the normal expected results. FIG. 17A shows the x-ray induced optical emission spectrum from a red-yellow (RY) phosphor combination. As compared to x-ray induced optical emission spectra of FIG. 12 (yellow; Y) and FIG. 9 (red; R), the spectrum of FIG. 17A showed a pronounced reduction in the emission around 500 nm. There also appeared to be the onset of unexpected emissions (although small) in the 300-400 nm wavelength range. These observations seem consistent with the results shown for red-yellow RY in both FIGS. 14 and 15 where substantial UV-driven reactions for red-yellow RY were observed.

Figure 17B:
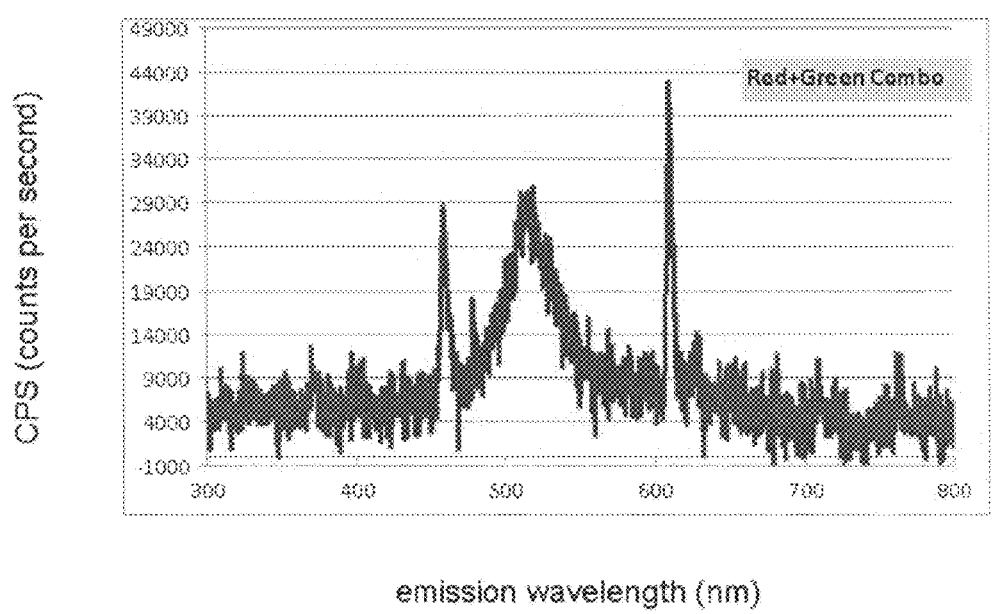
FIG. 17B is a depiction of an x-ray induced optical emission spectrum from a red-green RG phosphor combination.

Meanwhile, FIG. 17B is a depiction of another x-ray induced optical emission spectrum from a red-green RG phosphor combination, showing the onset of a feature around 290 nm. As compared to x-ray induced optical emission spectra of FIG. 10 (green; G) and FIG. 9 (red; R), the spectrum of FIG. 17B shows no unexpected change and does not appear to show the onset of emissions in the 300-400 nm wavelength range. This observation seems consistent with the results shown for red-green RG in FIGS. 14 and 15 where the measured results for UV-driven reactions with red-green RG were not substantially different than the control experiments.

However, some phosphor combinations such as red, yellow, green RYG show a prominent peak in the 280 to 300 nm range which may be contributing to the psoralen activation.

Figure 17C:
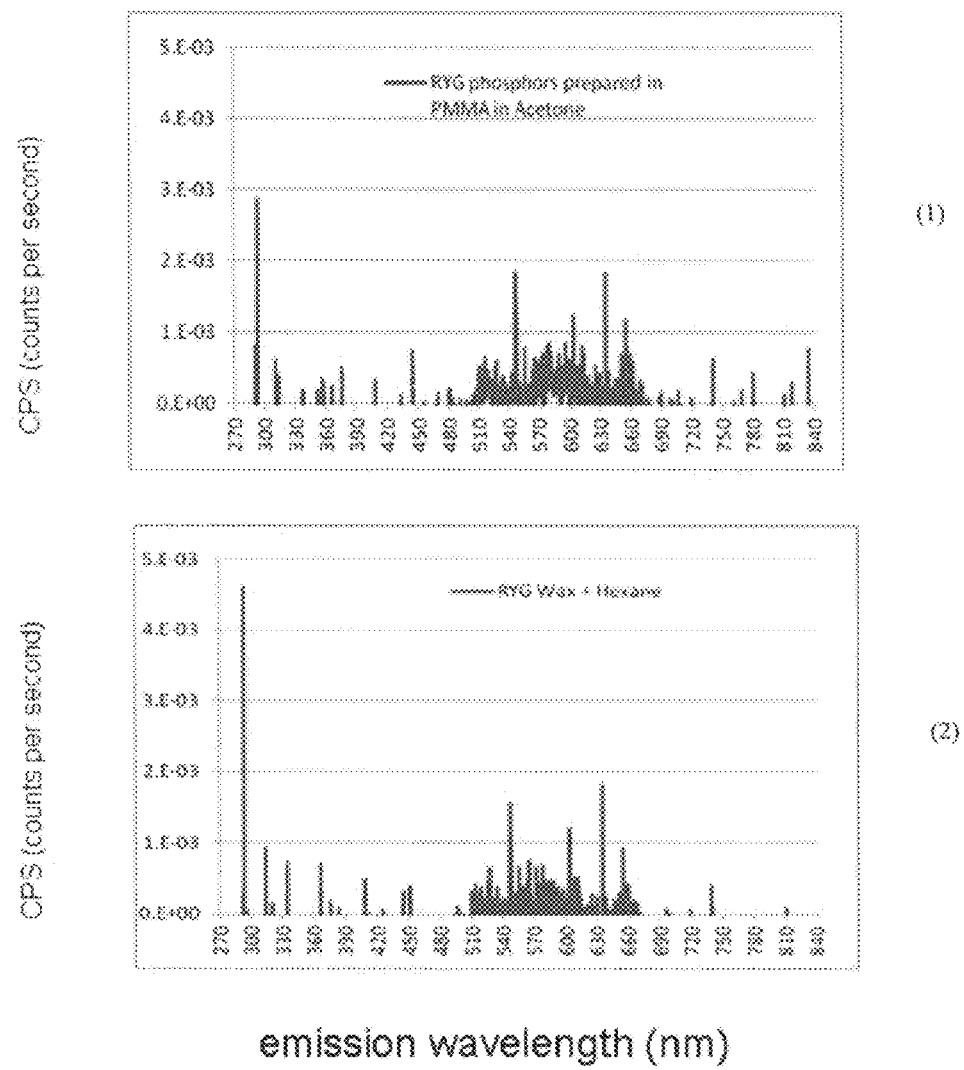
FIG. 17C is a depiction of an x-ray induced optical emission spectrum from a red-yellow-green RYG phosphor combination.

FIG. 17C is a depiction of an x-ray induced optical emission spectrum from a red-yellow-green RYG phosphor combination showing a prominent peak in the 280 to 300 nm range for solutions of red-yellow-green phosphors in acetone (1) and in hexane (2).

Medical Applications

Drug Activation

X-ray and other high energy radiation penetrate the human body. Upon their penetration into the body tissue, the energy modulation agents of this invention interact with the incident radiation to generate the secondary light (visible and/or ultraviolet light) as described above. As noted above, the secondary light can activate photoreactive drugs such as psoralen or other types of photoreactive drugs known to be activated by a UV and/or visible light source.

For example, in one embodiment of the invention, a material such as the yttrium oxide (or other phosphors or mixtures of phosphors as described above) is introduced into the body. Yttrium oxide as a host is known to be a down converter from X-ray radiation. In this particular example, X-ray incident radiation on the yttrium oxide will produce UV light which would in turn be used to activate drugs such as psoralen for the treatment of cancer. In this manner, a target organ having inside psoralen or other photoreactive drugs can be treated by irradiation with x-rays or other high energy sources, producing in turn visible and/or ultraviolet light for activation of the photoreactive drug.

Accordingly, in various embodiments, the present invention provides methods for the treatment of cell proliferation disorders, in which an initiation energy source (e.g., x-ray or other high energy source) provides an initiation energy that activates an activatable pharmaceutical agent to treat target cells within the subject. In one preferred embodiment, the initiation energy source is applied directly to the energy modulations agents whose light emission in turn activates the activatable pharmaceutical agent, preferably in proximity to the target cells. In one preferred embodiment, the initiation energy source is applied directly to the activatable pharmaceutical agent, preferably in proximity to the target cells.

Within the context of here, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the present invention. As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" (alternatively called a "photoactive agent" or PA) is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

A photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production or modulation of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include modulation of or releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent (e.g., light emitted from a predominantly visible-light emitting phosphor or a mixture of such phosphors).

An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention. Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD], alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photo sensitizers from which they are derived, and which preserve the function and substantial non-toxicity. Endogenous molecules are inherently non-toxic and may not yield toxic photoproducts after photoradiation.

The nature of the predetermined cellular change will depend on the desired pharmaceutical outcome. Exemplary cellular changes may include, but are not limited to, morphologic changes, apoptosis, necrosis, up-regulation of certain genes, down-regulation of certain genes, modulation of or secretion of cytokines, alteration of cytokine receptor responses, or a combination thereof.

The energy modulation agent may be preferably directed to the desired site (e.g. a tumor) by systemic administration to a subject. For example, a light-emitting energy modulation agent may be concentrated in the tumor site by physical insertion or by conjugating the light emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the light-emitting source in a specific target tumor.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

In a preferred embodiment, the photoactivatable agent, upon activation, binds to DNA or RNA or other structures in a cell. Other means for interaction of the photoactivatable agent with the DNA or RNA are possible, and this invention is not limited to any particular theory of interaction. Regardless, the activated energy state of the photoactivatable agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a photoactivatable agent to a patient, stimulates the photoactivatable agent to induce cell damage, and generates an auto vaccine effect.

Another advantage of using the visible phosphors and mixtures thereof is that side effects of UV induced damage can be greatly reduced by limiting the production of free radicals, singlet oxygen, superoxide, hydroxyl radicals, thiyl radicals, hydrogen peroxide, and other highly reactive groups that are known to damage healthy cells. Furthermore, additional additives, such as antioxidants, may be used to further reduce undesired effects of irradiation.

Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc.

Psoralen Activation

Accordingly, combinations of more than two "visible" phosphors can be used in this invention. Discussed below are x-ray settings and mass ratios for clonogenic cell kill experiments. F1 refers to the insertion of an aluminum filter into the x-ray beam to act as a filter.

| xRT settings (kvp/mA) | |
|---|---|
| LDLE | 20/20/F1, 30 seconds = 0.1 Gy |
| LDHE | 80/20/F1, 30 seconds = 0.2 Gy |
| HDHE | 80/20/F1, 2.5 minutes = 1.0 Gy |
| HDLE | 20/20/F1, 2.5 minutes = 0.5 Gy |
| Mass ratio | |
| 1a | Red/Yellow/Green (40/40/20) |
| 1b | Red/Yellow/Green (45/45/10) |
| 2a | Flamingo/Yellow/Green (40/40/20) |
| 2b | Flamingo/Yellow/Green (45/45/10) |

Psoralen is known to be activated by UV light in the range from 300 to 400 nm. Thus, a measure of cell kill would normally be assumed to be an indirect measure of the internal generation of UV light.

Figure 18A:
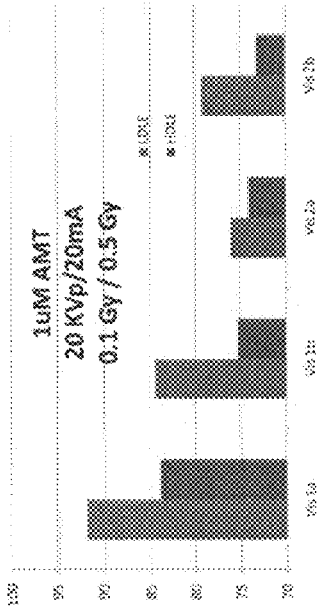
FIGS. 18A and 18B is a plotted cell kill comparison (shown here as the number of surviving colonies) between cancer cells treated with and without Psoralen (AMT) with different phosphor mixtures.
Figure 18B:
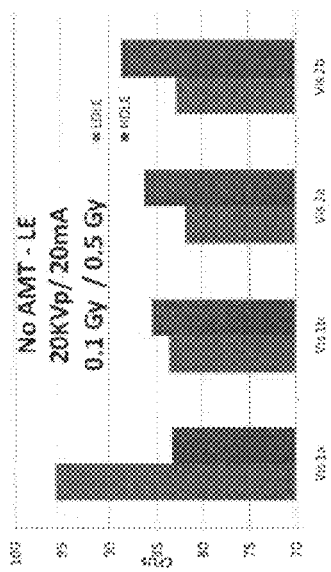

FIGS. 18A and 18B is a plotted cell kill comparison (shown here as the number of surviving colonies) between B16 cancer cells treated with and without psoralen (i.e., AMT) with different phosphor mixtures, but otherwise being x-ray stimulated and containing the multiple phosphor combinations noted above. On these drawings, LDLE=low xRT dose, low energy; HDHE=high xRT dose, high energy. Regardless of combination, the treatment with psoralen in all cases shows an improved cell kill.

Figure 19A:
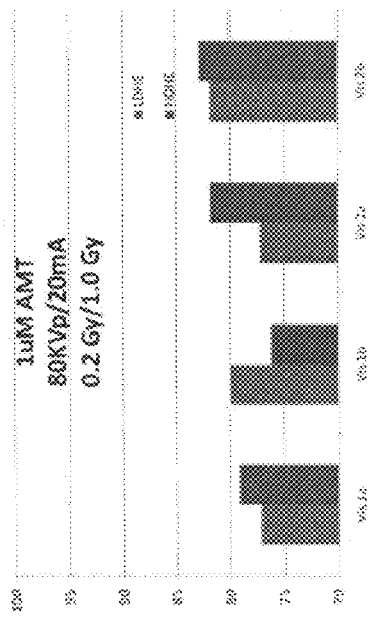
FIGS. 19A and 19B is a plotted cell kill comparison similar to FIGS. 18A and 18B at higher kVp x-ray conditions.
Figure 19B:
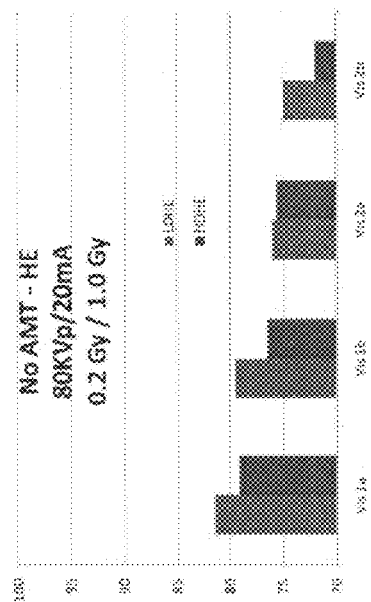

FIGS. 19A and 19B shows a similar comparison as in FIGS. 18A and 18B but at higher kVp x-ray conditions. On these drawings, LDLE=low xRT dose, low energy; HDHE=high xRT dose, high energy. Here, the comparisons of results between FIGS. 19A and 19B does not show an increased kill with psoralen present.

Figure 19C:
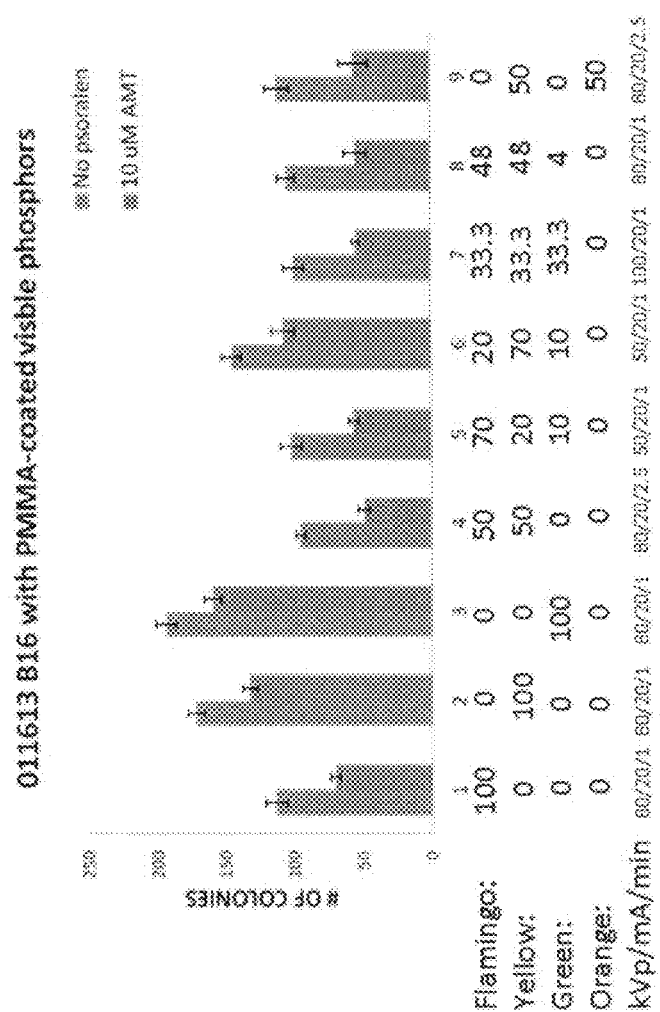
FIG. 19C is a depiction of the results from a clonogenic colony survival assay study utilizing a flamingo, yellow, green FYG phosphor combination in the presence and absence of psoralen (AMT)

FIG. 19C shows a clonogenic study utilizing a flamingo, yellow, green FYG phosphor combination. These results with and without Psoralen (i.e., the AMT) show a pronounced cell kill when the Psoralen is present.

Moreover, HPLC MS/MS analysis of synthetic (i.e. pdAdT) DNA samples after exposure to the x-ray activated multiple visible-light emitting phosphors of this invention showed the presence of mono-adducts of psoralen and in some cases psoralen cross-links with the DNA, consistent with the photoactivation of psoralen The tables below show these results and the capability of energy modulation agents having a normal predominant emission on one wavelength range producing changes in a medium expected to need activation from a different wavelength range.

| Poly-dAdT crosslinking data using "visible" phosphors | | | | | | | |
|---|---|---|---|---|---|---|---|
| Sample # | X-Ray Treatment | Time | 150 μL | Diluent | DNA | Mono-Adduct | Crosslink |
| 1 | 160 kvp, 20 mA | 4 min | G + R | PBS | Poly dAdT | 6.13E+03 | — |
| 2 | 160 kvp, 20 mA | 4 min | Y + R | PBS | Poly dAdT | 2.80E+03 | — |
| 3 | 160 kvp, 20 mA | 4 min | Y + R | H2O | Poly dAdT | 4.46E+03 | 1.61E+04 |
| 4 | 160 kvp, 20 mA | 4 min | G + R | H2O | Poly dAdT | — | — |

| Poly-dAdT crosslinking data using "visible" phosphors | | | | | | | |
|---|---|---|---|---|---|---|---|
| Sample # | X-Ray Treatment | Time | 100 μL | Diluent | DNA | Mono-Adduct | Crosslink |
| 1 | 160 kvp, 20 mA | 4 min | R + G | PBS | Poly dAdT | 1.85E+03 | |
| 2 | 160 kvp, 20 mA | 4 min | R + O | PBS | Poly dAdT | 1.78E+03 | |
| 3 | 160 kvp, 20 mA | 4 min | F + G | PBS | Poly dAdT | 8.75E+02 | |
| 4 | 80 kvp, 20 mA | 4 min | F + G | H2O | Poly dAdT | 6.87E+02 | |

The results with mixtures of two or more of the phosphors show the capacity for "visible emitting" phosphors of this invention to activate UV-sensitive compounds. This capability permits a wider range of phosphor combinations to be used which otherwise would have been dismissed (under conventional practice) as being useless for an UV-activated process.

Photo-Cage Activation

As described above, the energy modulation agents of a preferred embodiment of this invention (upon activation) can produce visible and/or ultraviolet light which (even for predominantly visible light emission) can open photocages designed for UV severance.

This unique capability permits the use of phosphors such as the red R phosphors or mixtures of the red-green RG, red-yellow RY, green yellow GY, etc to release a chemically active species from a photocage. Moreover, it is known in the art that excessive UV light exposure can degrade properties of the medium, such as UV degradation of the polymers or DNA "light poisoning."

Photocages such as nitrophenyl compounds photolyze with near-UV light centered at 350 nm, which lies in the UVA range (315-400 nm). Unlike UVB (280-315 nm) and UVC (100-280 nm), UVA is not absorbed by DNA appreciably and therefore does not directly cause DNA damage. A nitrophenyl compound as a photocage for Ca is shown below:

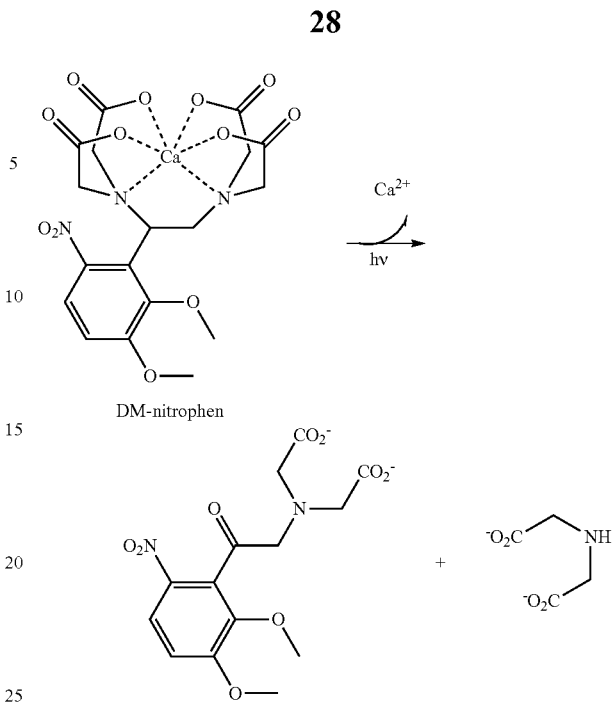

DM-nitrophen

Depending on the intensity of the light source, duration of exposure and cell type, however, UVA light can damage DNA and other cellular components indirectly via the formation of reactive oxygen species. Light toxicity can therefore be a serious limitation of these photocage compounds.

Hence, this preferred embodiment of the present invention which activates nominally UV activated photocages with predominantly visible light emitters (or emitters normally expected to have predominantly visible emissions) offers advantages when the medium being treated is particularly suspect to UV degradation.

Moreover, there already exist a number of metal photocages investigated for cancer treatment. Of these, cisplatin has been studied and known for its toxicity to both healthy and cancerous cells. $Pt^{IV}$ complexes are more inert to ligand substitution than their $Pt^{II}$ counterparts, and therefore must be reduced to their active $Pt^{II}$ form by extracellular and/or intracellular agents prior to reaction with DNA.

Workers have reported that, if the rate of reduction of $Pt^{IV}$ to $Pt^{II}$ can be increased at or around a tumor relative to normal tissue, then the effectiveness of the drug could be maximized. The [$PtCl_2I_2(en)$] complex photoreduces with visible light. While the photoproducts were not characterized, the resulting complex was shown to bind DNA. However, the unphotolyzed complex was also able to bind DNA, and there was no difference in cytotoxicity observed for cells kept in the dark as compared to those exposed to light. Accordingly, other Pt photocages were developed.

Cis,trans,cis-[$Pt(N_3)_2(OH)_2(NH_3)_2$] have been found to be stable in the presence of glutathione, and photolyzes into a complex that binds DNA and 5'-GMP. In addition, the photolyzed complex inhibits the growth of human bladder cancer cells as well as cisplatin-resistant cells, while cells treated with the complex and kept in the dark showed very little growth inhibition.

Accordingly, the present invention provides a mechanism by which mixtures of predominantly visible light emitters (or emitters normally expected to have predominantly visible emissions) can photoactivate (photolyze) Cis, trans, cis-[Pt(N$_3$)$_2$(OH)$_2$(NH$_3$)$_2$] without significant degradation and destruction of nearby healthy cells by high UV exposure or singlet oxygen generation.

Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

Certain wavelengths of light at certain intensities (delivered by laser, LED or another monochromatic source) will, for example, aid tissue regeneration, resolve inflammation, relieve pain and boost the immune system. The exact mechanism is still being explored and debated but it is agreed that the mechanism is photochemical rather than heat-related. Observed biological and physiological effects include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters).

U.S. Ser. Nos. 12/417,779 and 12/764,184 (the entire contents of which are incorporated herein by reference) describe non-invasive systems and methods for in-situ photobiomodulation. In these different approaches, a condition, disorder or disease in a subject is treated using an initiation energy source to induce a predetermined change in a target structure in a subject in situ to treat the condition, disorder or disease. The initiation energy sources in these applications generate internal light inside the subject to treat the condition, disorder or disease.

tobiomodulation effect, treating a condition, disorder or disease in the subject and therefore producing a change.

Commercial Applications

In the following commercial applications of the invention described here, the energy modulation agents 3 (e.g., luminescing particles or photon emitters) are provided and distributed into a medium 4 for deactivation or activation of agents in the medium to produce a physical, chemical, or biological change in the medium. In one embodiment, plasmonics agents as described above are added to the medium. The plasmonics agents can enhance both the applied initiation energy such that the enhanced initiation energy activates the at least one activatable agent which produces a change in the medium when activated and can enhance light converted by the energy modulation agents.

In a preferred embodiment, the energy modulation agents include down converters (such as for example phosphors which can convert x-ray or other high energy photon or particle into visible light. These down converters when used in combination can activate a variety of UV-stimulated photoreactions as well as activate any visible light activated reactions.

Examples of luminescing particles (down converters) can include gold particles (such as for example the nanoparticles of gold), BaFBr:Eu particles, CdSe particles, Y$_2$O$_3$:Eu$^{3+}$ particles, and/or other known stimulated luminescent materials such as for example ZnS:Mn$^{2+}$; ZnS: Mn$^{2+}$, Yb$^{3+}$, Y$_2$O$_3$: Eu$^{3+}$; BaFBr:Tb$^{3+}$; and YF$_3$:Tb$^{3+}$. More specific examples of the downconverters include, but are not limited to: BaFCl:Eu$^{2+}$, BaSO$_4^-$:Eu$^{2+}$, LaOBr:Tm$^{3+}$, YTaO$_4$, YTaO$_4$:Nb(*), CaWO$_4$, LaOBr:Tb$^{3+}$, Y$_2$O$_2$S:Tb$^{3+}$, ZnS:Ag, (Zn,Cd)S:Ag, Gd$_2$O$_2$S:Tb$^{3+}$, La$_2$O$_2$S:Tb$^{3+}$.

The embedded table below shows a listing of normally UV-emitting phosphors and their respective known peak emissions. Combinations of one or more of these phosphors with or without the "visible" phosphors described above can be used in this invention.

| | | Emission Spectrum | X-ray Absorption | | Microstructure | | |
|---|---|---|---|---|---|---|---|
| # | Phosphor | Peak Emission (nm) | Emiss Eff (%) | Eff (Z) | K-edge (keV) | Specific Gravity | Crystal Structure | Hygroscopic |
| 1 | BaFCl: Eu$^{2+}$ | 380 | 13 | 49.3 | 37.38 | 4.7 | Tetragonal | N |
| 2 | BaSO$_4$—: Eu$^{2+}$ | 390 | 6 | 45.5 | 37.38 | 4.5 | Rhombic | N |
| 3 | LaOBr: Tm$^{3+}$ | 360, 460 | 14 | 49.3 | 38.92 | 6.3 | Tetragonal | N |
| 4 | YTaO$_4$ | 337 | | 59.8 | 67.42 | 7.5 | Monolithic | N |
| 5 | YTaO$_4$: Nb (*) | 410 | 11 | 59.8 | 67.42 | 7.5 | Monolithic | N |
| 6 | CaWO$_4$ | 420 | 5 | 61.8 | 69.48 | 6.1 | Tetragonal | N |
| 7 | LaOBr: Tb$^{3+}$ | 420 | 20 | 49.3 | 38.92 | 6.3 | Tetragonal | N |
| 8 | Y$_2$O$_2$S: Tb$^{3+}$ | 420 | 18 | 34.9 | 17.04 | 4.9 | Hexgonal | N |
| 9 | ZnS: Ag | 450 | 17 | 26.7 | 9.66 | 3.9 | Hexgonal | N |
| 10 | (Zn,Cd)S: Ag | 530 | 19 | 38.4 | 9.66/26.7 | 4.8 | Hexgonal | N |
| 11 | Gd$_2$O$_2$S: Tb$^{3+}$ | 545 | 13 | 59.5 | 50.22 | 7.3 | Hexgonal | N |
| 12 | La$_2$O$_2$S: Tb$^{3+}$ | 545 | 12.5 | 52.6 | 38.92 | 6.5 | Hexgonal | N |

In this invention, the combination of energy modulation agents (luminescent particles or down converters, mixtures of down converters, up converters, mixtures of up converters, and combinations thereof as described above for example the mixtures of red, yellow, green, and/or blue phosphors noted above) would be provided inside a subject to be treated, and then activated by x-ray or some other source whose activation would be normally expected to produce light in a wavelength range which would not produce a photobiomodulation effect, but now upon exposure to the activation energy source would produce a pho- In addition to the inorganic compounds described here for down converters, organic compounds can be used to achieve the same purpose described in the current invention. Anthracene and anthracene based compounds can be used to achieve the objective of the invention (curing with no line of sight and thermal energy).

Anthracene exhibits a blue (400-500 nm peak) fluorescence under ultraviolet light. Furthermore, it was found that antharacene exhibits fluorescence under X-Ray energy. Anthracene light output was measured to be 40% to 50% of NaI(Tl).

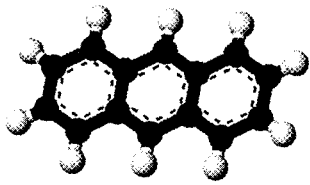

Various plastic scintillators, plastic scintillator fibers and related materials are made of polyvinyltoluene or styrene and fluors. These and other formulations are commercially available, such as from Saint Gobain Crystals, as BC-414, BC-420, BC-422, or BCF-10.

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Furthermore, the organic compounds that can convert X-ray to UV energy can be grafted (?) interwoven into synthetic polymer chains. These chains can be used as the base resin system for a cross-linking adhesive; hence leading to the formation of a new set of X-ray activatable resin systems.

A more extensive list of phosphors suitable for this invention is included below. Combinations of one or more of these phosphors with or without the "visible" phosphors described above can be used in this invention.

| Item # | Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|---|
| 24 | Zn3(PO4)2: Tl+ | 310 | | | | | | N |
| 33 | BaF2 | 310 | | | | | | Slightly |
| 30 | CsI | 315 | | | | | | N |
| 23 | Ca3(PO4)2: Tl+ | 330 | | | | | | N |
| 4 | YTaO4 | 337 | | 59.8 | 67.42 | 7.5 | Monolithic | N |
| 38 | CsI: Na | 338 | | | | | | Y |
| 14 | BaSi2O5: Pb2+ | 350 | | | | | | N |
| 27 | Borosilicate | 350 | | | | | | N |
| 34 | LaCl3(Ce) | 350 | | | | | | Y |
| 16 | SrB4O7F: Eu2+ | 360 | | | | | | N |
| 20 | RbBr: Tl+ | 360 | | | | | | ? |
| 15 | (Ba, Sr, Mg)3Si2O7: Pb2+ | 370 | | | | | | N |
| 17 | YAlO3: Ce3+ | 370 | | | | | | N |
| 37 | BC-422 | 370 | | | | | Organic | ? |
| 1 | BaFCl: Eu2+ | 380 | 13 | 49.3 | 37.38 | 4.7 | Tetragonal | N |
| 2 | BaSO4—: Eu2+ | 390 | 6 | 45.5 | 37.38 | 4.5 | Rhombic | N |
| 19 | BaFBr: Eu2+ | 390 | | | | | | ? |
| 36 | BC-420 | 391 | | | | | Organic | ? |
| 35 | BC-414 | 392 | | | | | Organic | ? |
| 25 | SrMgP2O7: Eu2+ | 394 | | | | | | N |
| 18 | BaBr2: Eu2+ | 400 | | | | | | N |
| 22 | (Sr, Ba)Al2Si2O8: Eu2+ | 400 | | | | | | N |
| 5 | YTaO4: Nb (*) | 410 | 11 | 59.8 | 67.42 | 7.5 | Monolithic | N |
| 21 | Y2SiO5: Ce3+ | 410 | | | | | | N |
| 6 | CaWO4 | 420 | 5 | 61.8 | 69.48 | 6.1 | Tetragonal | N |
| 7 | LaOBr: Tb3+ | 420 | 20 | 49.3 | 38.92 | 6.3 | Tetragonal | N |
| 8 | Y2O2S: Tb3+ | 420 | 18 | 34.9 | 17.04 | 4.9 | Hexagonal | N |
| 13 | Lu2SiO5: Ce3+ | 420 | | | | | | N |
| 26 | Lu1.8 Y0.2SiO5: Ce | 420 | | | | | | N |
| 9 | ZnS: Ag | 450 | 17 | 26.7 | 9.66 | 3.9 | Hexagonal | N |
| 29 | CdWO4 | 475 | | | | | | Slightly |
| 28 | Bi4Ge3O12 (BGO) | 480 | | | | | | N |
| 10 | (Zn,Cd)S: Ag | 530 | 19 | 38.4 | 9.66/26.7 | 4.8 | Hexagonal | N |
| 11 | Gd2O2S: Tb3+ | 545 | 13 | 59.5 | 50.22 | 7.3 | Hexagonal | N |
| 12 | La2O2S: Tb3+ | 545 | 12.5 | 52.6 | 38.92 | 6.5 | Hexagonal | N |
| 31 | Y3Al5O12 (Ce) | 550 | | | | | | N |
| 3 | LaOBr: Tm3+ | 360, 460 | 14 | 49.3 | 38.92 | 6.3 | Tetragonal | N |
| 32 | CaF2(Eu) | 435/300 | | | | | | N |

Furthermore, the luminescing particles (down converters, mixtures of down converters, up converters, mixtures of up converters, and combinations thereof) of the invention described here can be coated with insulator materials such as for example silica which will reduce the likelihood of any chemical interaction between the luminescing particles and the medium. For biological applications of inorganic nanoparticles, one of the major limiting factors is their toxicity.

Generally speaking, all semiconductor nanoparticles are more or less toxic. For biomedical applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable energy modulation agents which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

While many of the energy modulation agents of the invention are down conversion agents (i.e. where higher energy excitation produces lower energy emission), U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 including the ZnS as well as $Er^{3+}$ doped $BaTiO_3$ nanoparticles and $Yb^{3+}$ doped $CsMnCl_3$ are suitable in various embodiments of the invention.

Further, in various embodiments of the invention, up converters can be used in combination with the down converters (or mixtures of down converters) or in combination with various up converters. Various up converters suitable for this invention include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}M_{n_x}A_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\leq1$, $0<q\leq1$).

Indeed, some nanoparticles such as $ZnS:Tb^{3+}$, $Er^{3+}$; ZnS: $Tb^{3+}$; $Y_2O_3:Tb^{3+}$; $Y_2O_3:Tb^{3+}$, $Er^{3+}$; $ZnS:Mn^{2+}$; ZnS:Mn, $Er^{3+}$ are known in the art to have two functions, capable of functioning for both down-conversion luminescence and upconversion luminescence.

To reduce the toxicity or to make these nanoparticles bio-inert or biocompatible, one embodiment of the invention described here coats these nanoparticles with silica. Silica is used as a coating material in a wide range of industrial colloid products from paints and magnetic fluids to high-quality paper coatings. Further, silica is both chemically and biologically inert and also is optically transparent. Other coatings suitable for this invention include a polymethyl methacrylate (PMMA) coating and an ethyl-cellulose coating.

In one embodiment of this invention, luminescing particles (down converters, mixtures of down converters, up converters, mixtures of up converters, and combinations thereof) in encapsulated structures could be placed in the vicinity of the medium. In one embodiment for the invention described here, luminescing particles are coated on the interior of quartz or glass tubes and sealed. In another embodiment, luminescing particles could be coated on the surface of spheres or tubes, and afterwards encapsulated with silica (or other suitable passivation layer) using a vapor deposition or sputtering process or spin-on glass process of the solution process described above to make the encapsulation structures which may be part of re-entrant structures extending from walls of a container or which may be part of a fluidized bed structure. In another embodiment, the plasmonics agents are fixed to an outer surface of the glass tubes. External light applied to the tubes and scattered to the outer surfaces is enhanced at the plasmonics agents permitting more efficient treatment of the medium without necessarily having to use energy modulation agents.

Sterilization and Cold Pasteurization of Fluids

It is known that ultraviolet (UV) with a wavelength of 254 nm tends to inactivate most types of microorganisms. The invention described herein provide in one embodiment a configuration where energy modulation agents can be placed inside fixtures such as quartz or glass within the fluid medium (water, fruit juices, dairy products, etc) and irradiated with x-rays (or other penetrating radiation) through for example a plastic or aluminum container to activate the energy modulation agents in the fluid medium with internally generated visible and/or ultraviolet light. As such, the expense and fragility of a conventional sterilization reactor constructed from glass of other similar structure can be avoided.

While discussed with regard to water, fruit juices, dairy products, etc, any other medium to be sterilized including food products, medical products and cosmetic products could be treated using the technique of the invention described herein.

Sterilization of Medical and Pharmaceutical Articles

Gamma irradiation has been used conventionally to sterilize medical bottle caps and other medical, pharmaceutical, and cosmetic articles such as surgical disposables (e.g., surgical bandages, dressings, gauze pads, nappies, delivery kits, and etc.), metallic products (e.g., surgical blades, implants, aluminum caps, containers, etc.), and plastic and rubber Items (e.g., petri-dish, centrifuge tube, blood collection sets, scalp vein sets, shunt valves, rubber gloves, contraceptive devices, gowns, wraps covers, sheets, etc.). The invention would be applicable for the sterilization of any "interior" surfaces of these and other products.

In one embodiment of the invention described herein, luminescent particles (or down converters, mixtures of down converters, up converters, mixtures of up converters, and combinations thereof) would be included in an adhesive layer when the seal material is applied to the bottle cap. X-ray irradiation would then be capable of curing the adhesive (if for example the adhesive were a photosensitive adhesive as discussed below in greater detail) and would produce within the adhesive medium visible and/or ultraviolet radiation for sterilization or for the production of singlet oxygen or ozone for biological germicide. Additionally, plasmonics agents can be included to enhance the effect of the incident radiation or the internally generated (visible and/or ultraviolet) radiation.

While illustrated here with regard to medical bottle caps, other adhesively constructed devices could benefit from these procedures in which the adhesive medium is cured and/or sterilized during activation of energy modulation agents.

Sterilization of Blood Products

U.S. Pat. No. 6,087,141 (the entire contents of which are incorporated herein by reference) describes an ultraviolet light actved psoralen process for sterilization of blood transfusion products. Here, this invention can be applied for the treatment of or the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. These photoactivatable agents are introduced into the blood product (or a patient's blood stream). A penetrating energy is applied to the blood product (or to the patient). The down converters, mixtures of down converters, up converters, mixtures of up converters, and combinations thereof (either included in the blood product) or in encapsulated structures generate secondary light (visible and/or ultraviolet) which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a bloodborne germicide is treated by the psoralen, the coumarin, or the derivative thereof.

Low kVp Systems

PCT application PCT/US12/45930 (the entire contents of which are incorporated herein by reference) describes a system for light stimulation within a medium. The system in the '930 application has a reduced-voltage x-ray source configured to generate x-rays from a peak applied cathode voltage at or below 105 kVp, and a first plurality of energy-emitting particles in the medium which, upon radiation from the x-ray source, radiate at a first lower energy than the x-ray source to interact with the medium or with at least one photoactivatable agent in the medium.

The x-ray induced emissions noted above represent merely one example of a class where stimulated emission from a combination of energy modulation agents yields unexpected frequencies of emitted light. In one embodiment of this invention, the above-noted energy modulation agents (and combinations thereof) can be used in low kVp systems to activate psoralen and its derivatives.

Additionally, certain phosphors/phosphor combinations may have different excitation optima for emission. Furthermore, certain phosphors/phosphor combinations may have show increased emissions or an increased effect when the x-ray energy (kVp) of the beam is lowered.

Sterilization Methods and System Components

Optical techniques have been often used in sterilization procedures to render unwanted or harmful waterborne microorganisms incapable of reproducing using ultraviolet light (specifically the spectral area of UV-C, 200 to 280 nm range). Ultraviolet light in the UV-C is considered the most lethal range as a germicidal disinfectant (capable of altering a living microorganism's DNA, and keeping the microorganism from reproducing). UV-C, with 264 nanometers being the peak germicidal wavelength, is known as the germicidal spectrum. Although the UV-C method is simple and effective, it is not particularly effective in samples (gas, liquids, particulates) enclosed on containers which do not transmit UV light. The present invention provides techniques and systems that can use externally applied radiation such as X-ray for sterilization. While illustrated below with respect to X-ray irradiation, and as discussed above, other suitable forms of energy could be used provided the containers and medium to be sterilized was sufficiently transparent for the medium to be thoroughly irradiated. Examples of alternative sources and materials for upconverting luminescence to higher energies have been discussed above.

Figure 20:
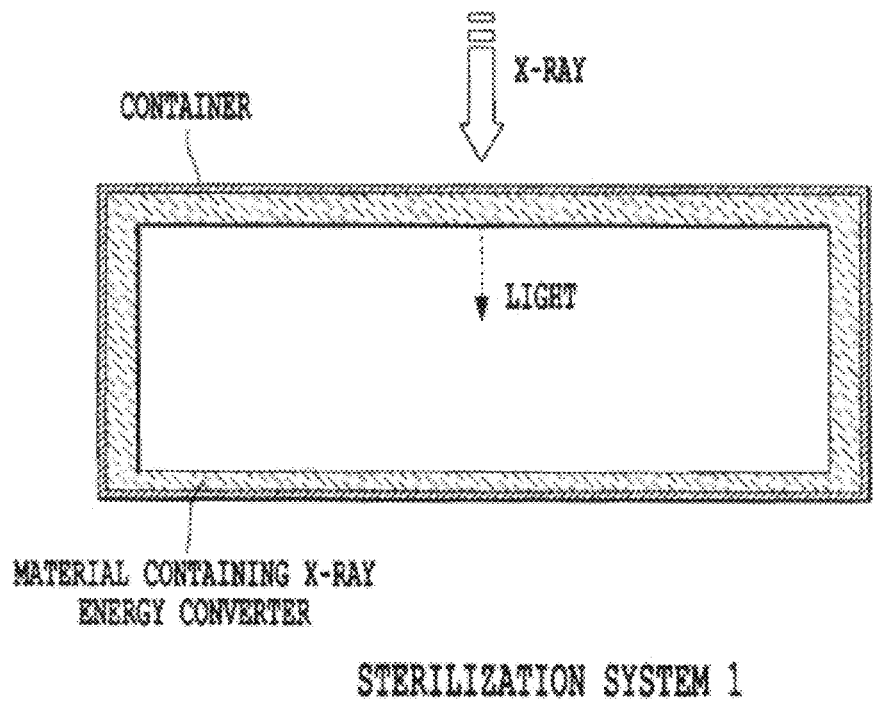
FIG. 20 is a representation of an embodiment of a sterilization system of the invention.
Figure 21:
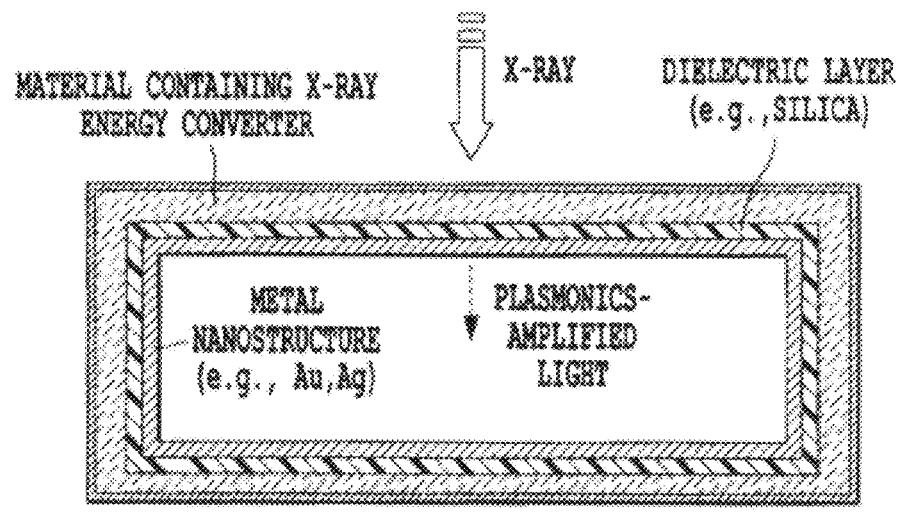
FIG. 21 is a representation of another embodiment of a sterilization system of the invention.
Figure 22:
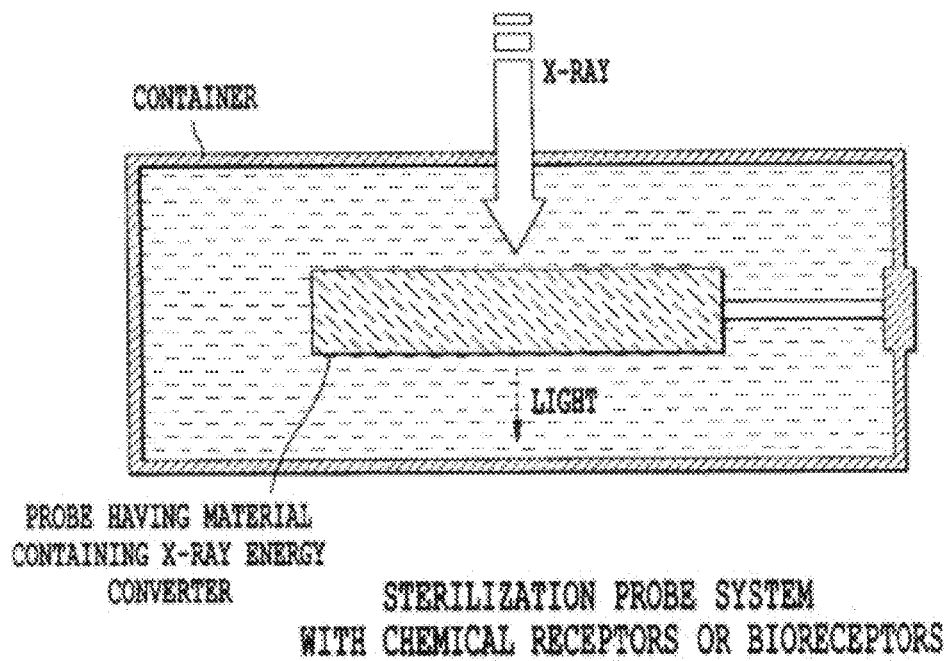
FIG. 22 is a representation of another embodiment of a sterilization system of the invention.

FIGS. 20-22 show various embodiments of sterilization systems and probes that can be used with X ray excitation. More systems are described in U.S. Ser. No. 12/401,478 now U.S. Pat. No. 8,376,013, the entire contents of which are incorporated herein by reference. These systems are applicable in a number of the applications discussed above and as well as in other sterilization areas. The systems could thus be used in the waste water detoxification, blood sterilization, cold pasteurization, and photodeactivation commercial applications discussed in the sections above. These systems show the use of artificial containers in which the medium to be treated is disposed.

FIG. 20 shows one embodiment of a sterilization system of the invention that includes: a container and a material containing an X-ray energy converter. The container holds a sample to be sterilized (e.g., liquid, gas, or particulates). X-ray radiation, capable of penetrating the container wall, excites the material containing the X-ray excitation energy converter (EEC), which is configured to emit emission light. The EEC material is selected such that the emitted or luminescence light occurs in a spectral region that can be used for sterilization (e.g., the ultraviolet spectral range).

FIG. 21 shows one embodiment of another sterilization system of the invention that utilizes plasmonics and includes: a container, a material containing an X-ray energy converter, a dielectric layer (e.g., silica), and a metal nanostructure (e.g., Au, Ag). The container holds a sample to be sterilized (e.g., liquid, gas, or particulates). X-ray radiation, capable of penetrating the container wall, excites the material containing the X-ray excitation energy converter (EEC), which in turn emits emission light. The EEC material is selected such that the emitted or luminescence light occurs in a spectral region that can be used for sterilization (e.g., an ultraviolet spectral range). The metal nanostructure is designed to amplify the luminescence light due to the plasmonics enhancement effect discussed above. The dielectric layer is designed to separate the material of the X-ray energy converter from the metal nanostructure in order to minimize or prevent possible quenching of the luminescence. The optimal thickness of the dielectric layer is about 1 to 5 nm such that the dielectric layer does not significantly alter the plasmonics effect.

FIG. 22 shows an embodiment of a sterilization probe system of the invention that includes a container which can hold the medium to be sterilized and a probe made of material containing an X-ray energy converter. The sample inside the container can be liquid, gas, or particulates. X-ray radiation, capable of penetrating the container wall, excites the probe having the material containing X-ray excitation energy converter (EEC), which in turn emits emission light. The EEC material is selected such that the emitted or luminescence light occurs in a spectral region that can be used for sterilization (e.g., the ultraviolet spectral range). The probe can be removed and reinserted into the container and reused.

In general, without limitation to the sterilization systems discussed above, in one aspect of the invention, there is provided a system for producing a change in a medium disposed in an artificial container. The system includes a mechanism configured to provide to the medium 1) an activatable agent and 2) at least one energy modulation agent, The energy modulation agent is configured to emit light into the medium upon interaction with an initiation energy. The system includes an initiation energy source configured to apply the initiation energy to the medium. The energy modulation agent has a normal predominant emission of radiation in a first wavelength range (WR1) outside of a second wavelength range (WR2) known to produce the change, but under exposure to the applied initiation energy produces the change.

Waste Water Detoxification

Photocatalysis has also been used as tertiary treatment for wastewater to comply with the regulatory discharge limits and to oxidize persistent compounds that have not been oxidized in the biological treatment. Photocatalysis has being applied to the elimination of several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, $WO_3$, and ZnS, have been studied, but the best results have been achieved with $TiO_2P_{25}$. These photocatalyst are usable for the invention described here.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

In the invention described herein, down converters, mixtures of down converters, up converters, mixtures of up converters, and combinations thereof would be placed inside quartz or glass fixtures within the waste water or would be placed on silica encapsulated structures within the waste water which, like the photocatalytic $TiO_2$, could be entrained in the waste water during the irradiation. Additionally, the plasmonics agents can be included to enhance the effect of the incident radiation or the internally generated radiation.

Upon irradiation with x-rays (or other penetrating radiation) through for example a plastic or aluminum container, activation of the luminescing particles (down converters, mixtures of down converters, up converters, mixtures of up converters, and combinations thereof)) would generate secondary light (visible and/or ultraviolet) in nearby presence of the photocatalytic agent. In other words for the invention described herein, the down converters, mixtures of down converters, up converters, mixtures of up converters, and combinations thereof (i.e., energy modulation agents) are mixed along with the photocatalytic semiconductor particles in the waste water fluid stream, and the exterior activation energy source penetrates the container (e.g., a plastic or aluminum container) and irradiates the bulk of the waste water, producing visible and/or UV light throughout the waste water which in turn drives the photocatalytic reactions. In one embodiment, the plasmonics agents are complexed with the luminescent particles or other energy modulation agents prior to being added to the fluid stream.

As such, the invention described herein offers a number to advantages over that described above, including the elimination of expensive holding tanks for the waste water, the avoidance of having to pump the wastewater at higher pressures or flowrates to produce sufficient turbulence, and the generation of UV light throughout the wastewater to thereby provide faster bulk processing of the waste water.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

UV irradiation is known to affect graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of down converters, mixtures of down converters, up converters, mixtures of up converters, and combinations thereof (serving as energy modulation agents) in dispersion in the fluid medium being used for photostimulation. Additionally, the plasmonics agents can be included to enhance the effect of the incident radiation or the internally generated radiation. In one embodiment, the plasmonics agents are complexed with these energy modulation agents prior to being added to the fluid medium.

Upon irradiation with x-rays (or other penetrating radiation) through for example a plastic or aluminum container, activation of the luminescing particles (i.e., energy modulation agents) would generate visible and/or UV light throughout the volume of the medium (eliminating any shadowing effects) and permitting batch or bulk type processing to occur in parallel throughout the container.

In other examples, the interior generation of light (visible and/or ultraviolet) inside a bulk medium may serve to stimulate a chemical or biological process either by interaction of the light (visible and/or ultraviolet) with activatable agents in the medium or the indirect generation of heat which the invention described here by way of dispersed energy modulation agents would provide a controlled and uniform way to heat a vat of material in a biological or chemical process.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above for liquid pasteurization could be used here. For non-liquid products, energy modulation agents (down converters, mixtures of down converters, up converters, mixtures of up converters, and combinations thereof) with little and preferably no toxicity (e.g. Fe oxides or titanium oxides) could be added. External activation would result in the generation of visible and/or ultraviolet light within the liquid. Here, the concentration of these additives would likely be limited by any unexpected changes in taste.

Photoactivated Cross-linking and Curing of Polymers

In another embodiment of this invention, a system for curing of a radiation-curable medium includes 1) a mechanism configured to supply an uncured radiation-curable medium including an activatable agent and at least one energy modulation agent into the uncured radiation-curable medium and 2) an initiation energy source configured to apply an initiation energy throughout a region including the uncured radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

In this application, energy modulation agents (down converters, mixtures of down converters, up converters, mixtures of up converters, and combinations thereof) are provided and distributed into an uncured polymer based medium for the activation of photosensitive agents in the medium to promote cross-linking and curing of the polymer based medium. Additionally, the plasmonics agents can be included to enhance the effect of the incident radiation or the internally generated radiation. The plasmonics agents can be complexed with the luminescent particles or other energy modulation agents prior to being added to the polymer.

As noted above, for adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the luminescing particles (or energy modulation agents) are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with for example carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (.eta.sup.5-2,4-cyclopentadien-1-yl)-bis[2,6-difluoro-3-(1H-pyrrol-1-yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

It will be appreciated that the most efficient curing system will be one in which the particular photo-initiator is selected based on its absorption, its photo-catalysis sensitivity to the intensity of the incident radiation (i.e.; the efficiency of energy transfer).

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 urn. Other Q-CEL products are shown below in tabular form. Another commercially available hollow glass microsphere is sold by Kish under the trade name SPHEREICEL. SPHEREICEL 110P8 has a mean particle size of about 11.7 microns, and a crush strength of greater than 10,000 psi. Yet other commercially available hollow glass microspheres are sold by the Schundler Company, Metuchen, N.J. under the PERLITE tradename, Whitehouse Scientific Ltd., Chester, UK and 3M, Minneapolis, Minn. under the SCOTCHLITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, conventional silicone and polymeric adhesive or release or coating compositions are prepared using conventional mixing, heating, and incubation techniques. Included in these conventional compositions are luminescing particles. These luminescing particle containing compositions can then be applied to surfaces of objects to be fixed together or to surfaces where a hard coating is desired or cast in a curable form for the production of molded objects. The luminescing particles in these compositions upon activation will produce radiant light for photoactivated cure of the luminescing particle containing polymer composition. The density of luminescing particles in these compositions will depend on the "light transparency" of the luminescing particle containing composition. Where these compositions contain a significant amount of the inorganic filler as discussed above, the concentration of luminescing particles can be reduced for example as compared to a composition with a black color pigment where the light transparency will be significantly reduced.

One advantage of the invention described here as seen from this example is that color pigments can be included in the light curable resins without significant compromise in the cured product performance. These color pigments may include one or more colored pigments well known to those of ordinary skill in the art. Such pigments are generally metal oxides and include, but are not limited to, titanium dioxide, iron oxides, organic complexes, mica, talc and quartz. One pigment may be used, or a combination of two or more pigments may be utilized. Different colors can be obtained by choosing proper pigments and combining them in a similar fashion as set forth in the following examples with the necessary adjustments, common in the paint industry, being made. Accordingly, in one embodiment of the invention, these color pigments including carbon black may also be included as an optically opaque materials to limit the propagation of internally generated light from the point of generation.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, energy modulation agents (down converters, mixtures of down converters, up converters, mixtures of up converters, and combinations thereof) described above are added to these Bach et al. compositions, optionally including in one embodiment various color pigments. Due to the fact that the exterior energy source penetrates throughout the entirety of the Bach et al. compositions, thicker surface coatings can be realized. Further, the coatings can be applied to intricate surfaces having for example been prepared with recesses or protrusions. Curing with the recesses and around the protrusions without being limited by conventional UV shading will likely provide enhanced adherence of the surface coating to the work piece.

Moreover, in one embodiment of the invention, an external energy source of the initiation energy can be directed to a structural element in which a gap (or crack) therein was filled with an uncured radiation-curable medium (such as those described above). The internally generated light will cure or promote curing of the uncured radiation-curable medium in the gap (or crack) thereby providing a repair to the structure being irradiated.

Presently, there are available commercial epoxy systems which utilize epoxy resin injection for the structural restoration of concrete. Epoxy injection is very often the only alternative to complete replacement of a structure. It therefore results in great cost savings. Besides filling the cracks, epoxy injection is known to protect rebar in the concrete and to stop water leakage. Commercially, the epoxy injection resin provides a system for welding cracks which restores the original strength and loading originally designed into the concrete. Typically, low viscosity resins are pressure injected into the cracks. Often holes are drilled near or into the cracks to provide a conduit for pumping the resin into the cracks.

It, however, takes time for the resin to penetrate into the thinner, even hair line cracks. Unfortunately, time is limited in the present commercial systems due to the fact that the resins are premixed with hardeners whose time to cure sets an upper limit for how long the low viscosity resin can flow into the cracks. Furthermore, time to complete repair is an issue in many industrial repairs as the hardener is usually present in a concentration high enough to have the resin set for example in twenty four (24) hours. Moreover, with traditional resin methods, it is not possible to induce curing at specific regions of interest since all the areas of the resin will be cured.

The present invention offers a number of advantages. Firstly, the resin of the present invention will be a photactivated resin which will not substantially cure until the x-ray source generates internal light (visible and/or ultraviolet) to activate the photoinitiators. This provides more flexibility in pumping and waiting for complete crack fill. Secondly, once the photoactivatable resin is in place, its cure is then activated, and the cure occurs at a rate not controlled by the convention hardening reaction. Thirdly, the x-ray penetration through the concrete and the crack region will provide a more uniform mechanism for cure of the resins, with the deep cracks being as likely to fully cure as the narrow cracks which may extend deeper into the material. Furthermore, the present invention allows the possibility to cure only the specific areas of interest, i.e., where the X-ray is irradiated.

In another embodiment of the present invention, the external energy source can be a directed or focused beam of the initiation energy which cures an uncured radiation-curable medium to produce a patterned element. In this embodiment, the structure holding or at least partially enclosing the uncured radiation-curable medium can be a structure opaque to visible light. In this manner, the uncured radiation-curable medium (which normally would be photoactivated upon exposure to ambient light) can be transported without premature curing. In this embodiment, the curing would be activated for example by directed one or several focused beams of x-rays whose overlap generates regions in the structure holding or at least partially enclosing the uncured radiation-curable medium where the generated UV or visible light from the energy modulation agents in the medium would be of sufficient intensity to activate the photoinitiators.

In this manner, precise three-dimensional and two-dimensional patterning can be performed. In this manner, a number of differently sized and different materials can be adhered to each other.

In general, in this aspect of this invention, a radiation-curable medium can be cured by applying an initiation energy throughout a composition comprising 1) an uncured radiation-curable medium and 2) at least one energy modulation agent. The initiation energy interacts with the energy modulation agent to directly or indirectly cure the uncured medium by polymerization of polymers in the medium. The method includes curing the radiation-curable medium by activating a photoinitiator in the radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

Thus, in one embodiment, the present invention provides a radiation-curable article including a radiation-curable medium and at least one energy modulation agent distributed throughout the medium. The energy modulation agent being a substance which is capable of converting initiation energy to a light capable of curing the radiation-curable medium by polymerization of polymers in the radiation-curable medium. The energy modulation agent has a normal predominant emission of radiation in a first wavelength range (WR1) outside of a second wavelength range (WR2) known to cure the radiation-curable medium, but under exposure to the applied initiation energy cures the radiation-curable medium.

Working Examples

To demonstrate the present invention, an adhesive chemistry was made adding 75% by weight of PUMA 92-056 (from Rahn Corp) to 20% of TriMethyl-Trimethylolpropane-Trimethacrylate (TMPTMA) from BASF and a 5% by weight of photo-initiator Darocur 1173 from BASF. The chemistry was mixed with various phosphors (described below) ranging from 6% by weight to 20% by weight. The mixture was then stirred thoroughly and stored in a light-tight container.

There were three sets of phosphors evaluated. The first set of phosphors included a 50%-50% mixture of the Flamingo-phosphor and the Green-Phosphor. The second set of phosphors consisted of a 50%-50% mixture of the Red-phosphor and the Yellow-Phosphor. The third set of phosphors consisted of a 25% of the Red-phosphor, 25% of the Yello-phosphor, 25% of the Flamingo-phosphor, 25% of the Green-phosphor.

Furthermore, a fourth set of phosphors included a mixture of 50% of LaOBr and 50% of YTaO4. The fourth set of phosphors were phosphors that emit in the UV regime.

The adhesive/phosphor mixtures (about 0.2 grams) were placed between two glass slides and cured under x-ray exposure. The x-ray energy was set at 160 kVp and 20 mA and the distance from the X-Ray source was set at 10 cm.

The adhesives loaded with the UV emitting phosphors cured in 2 minutes under this x-ray setting. All of the other adhesives loaded 12.5% by weight with the three different set of phosphor combinations cured in 2.5 minutes. The cured adhesive was qualitatively similar regardless of the "visible" or "ultraviolet" phosphors used.

Furthermore, a commercial adhesive system was modified by adding the appropriate amount of phosphor mixtures to ACU-TITE UV106G. This adhesive system contains by weight percent the following components: Acrylate oligomers 30-50%, Acryate esters 40-60%, Substituted acrylate 1-10%, SILICA, AMORPHOUS, FUMED, 0.1-3%, Photoinitiators 1-5% and Adhesion promoter 0.1-1.5%. This adhesive was loaded with the Flamingo-Green phosphor mixture using 12.5% and cured in the x-ray. The cure was under 1 min at 160 kVp, 20 mA when the sample was positioned at a distance of 1 cm.

The UV phosphors have a much higher light intensity output than the "visible" phosphors. Yet the "visible" phosphor mixture cures in about the same amount of time and with approximately the same quality of cure as the UV phosphor-adhesive mixture. Controls with no phosphors of any kind showed no curing under x-ray exposure.

Patterned Element Curing

As an example in another embodiment, a patterned element such as a device (such as plug to close a specific internal hole or path ways) can be fabricated (e.g., cured) inside structures (e.g., building materials, man-made or natural underground storage tank, internal organs of human body, etc) using energy excitation (e.g., X ray) from the outside of such structures. Another application of this technique would involve the fabrication of orthopedic structures inside the body, where the curable resin was introduced locally at the point of the orthopedic structure to be formed and a directed or focused x-ray beam cured the structure.

Accordingly, in another embodiment of the present invention, there is provided a method (and associated system) for producing a patterned element inside a structure. The method places inside the structure a radiation curable medium including at least one of a plasmonics agent and an energy modulation agent (down converters, mixtures of down converters, up converters, mixtures of up converters, and combinations thereof). The energy modulation agent is configured to emit light into the medium upon interaction with an initiation energy. The method applies to the medium the initiation energy from a directed or focused energy source. The applied initiation energy interacts with the plasmonics agent or the energy modulation agent to generate light (visible and/or ultraviolet) at local regions inside the structure to cure locally the radiation curable medium.

As noted above, this method can form for the patterned element a plug to close a hole or pathway in the structure such as for example holes or pathways in a building material, a man-made or natural underground storage tank, or an internal organ in a human or animal body. The method can form for the patterned element a prosthetic device at a local point in the body of a human or animal.

The method can further localize the curing by placing in the radiation curable medium optically dense materials (such as the color pigments discussed above) to reduce propagation of the generated light from the point of generation.

Security and Product Tagging

In one embodiment of this invention, the x-ray induced emissions are used for security tags on wide variety of products including piracy tags associated with product identification. U.S. Pat. No. 8,389,958 (the entire contents of which are incorporated herein by reference) describe in one embodiment, applications areas such as security and tagging operations where a primary light source, for example a NIR beam is focused and directed onto a target object. Applications of the above-noted energy modulation agents described in this invention would permit enhanced coding in areas such as for example: (i) detecting and removing of counterfeit currency from circulation, (ii) detecting and removing of counterfeit adulterated products (e.g., fake drugs), (iii) tracing the origin of products (e.g., alcohol, tobacco, firearms) and commodities (e.g., oil/gas tag and trace), (iv) tagging controlled substances (e.g. military explosives) or restricted technology (e.g. nuclear and communications technologies), (v) marking single source, high value commodities (e.g., specialty fibers), and (vi) brand protection, and (vii) verifying the authenticity of documents, financial instruments (e.g. bearer bonds), and various forms of identification.

With UV incident on the above-noted energy modulation agents (and combinations thereof), emissions in the visible wavelength range could be used as a first pass screening that the product identifier was in place and for example to conclude that the product marking was proper. The UV illuminated mark could contain for example a passcode which the inspector would recognize.

Upon inspection, for example in a closed x-ray system, an x-ray beam incident on the above-noted energy modulation agents (and combinations thereof) would produce x-ray induced emissions in the ultra-violet or visible wavelength range which would then be detected and analyzed for authentication. These inspection techniques would be similar to those noted in U.S. Pat. No. 8,389,958, except that here it would require knowledge of the "secret" combination of energy modulation agents (e.g., phosphors) to properly see a product-identifying wavelength or to read a characteristic signature.

In conventional bar coding operations, a scanner is used to essentially read a series of black and white lines with the density and spacings being indicative of a particular coded item. In this invention, these printed bar codes could make use of the energy modulation agents (and combinations thereof) described above which offer the possibility of a multicolor emission from either x-ray (down-converting), ultraviolet (down-converting), or infrared (up-converting) sources.

Thus, the amount of information that can be encoded into a traditional bar code area may be greatly increased. For example, a specific color categorization could introduce completely different encodings for what would normally be the same series of black and white lines. Further, since many products are routinely inspected by x-ray analysis, this inspection process with the tags of this invention using the above-noted energy modulation agents (and combinations thereof) could in addition verify the manufacturer or packager for product tracking, safety, and monitoring.

In these tagging and labeling applications, the invention provides a system for identification of an object. The system includes a readable medium (e.g., a paper product, a plastic product, and a glass product which may be a part of a security tag or a bar code on any product), a particle acting as an energy modulation agent included in or on the surface of the readable medium. The particle (i.e., the energy modulation agent) is configured to emit radiation into the medium or body upon interaction with an initiation energy. The energy modulation agent has a normal predominant emission of radiation in a first wavelength range (WR1) outside of a second wavelength range (WR2). In this embodiment, information concerning the product is encoded in the second wavelength range (WR2).

Color Enhancement

In one embodiment of this invention, the x-ray induced emissions noted above represent merely one example of a class where stimulated emission from a combination of energy modulation agents yields unexpected frequencies of emitted light (i.e., producing a change or enhancement in the color of the medium). U.S. Ser. No. 13/204,355 (the entire contents of which are incorporated herein by reference) describes systems for generating or enhancing light emission or reflectance from visible displays and colored surfaces so as to enhance the appearance of the visible object. In the '355 application, a light emitting composition included first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color was enhanced relative to reflected white light without emission from the first and second color emitters.

Here, with the above-noted energy modulation agents (and combinations thereof), additional light enhancement would occur if the colored surfaces were exposed to an initiating radiation, such as x-rays (as in the product security tagging application described above). However, the above-noted energy modulation agents (and combinations thereof) do not in combination always produce the expected simple emission results. While not bound to any particular theory, it is possible that the mechanism of emission, absorption, and re-emission changes the resultant "color" output. Thus, the combination of phosphors with their normally predominant emission at different distinctive wavelengths may have at least their relative strengths changed and altered (i.e., changes in extent, intensity, spectral width, etc). For the human eye, the relative strengths are integrated.

Hence, a combination of the phosphors described above may well enhance a particular color band relative to what color the eye would see for the colored surface had the colored surface not have had included the above-noted energy modulation agents (and combinations thereof). The combination of phosphors of this invention would be useful in paint, inks, displays, signs, pigments, cosmetics, fabrics, apparel, etc.

Solar Cell Conversion

As noted above, the x-ray induced emissions noted above represent merely one example of a class where stimulated emission from a combination of energy modulation agents yields unexpected frequencies of emitted light. In one embodiment of this invention, the above-noted energy modulation agents (and combinations thereof) can be used to promote matching of the solar spectrum to the spectral efficiency of a solar photoconversion cell, as described for example in U.S. Ser. No. 12/891,466 (the entire contents of which are incorporated herein by reference). As explained in the '466 application, photons with an energy below the band gap of the absorber material cannot generate a hole-electron pair, and so their energy is not converted to useful output and only generates heat if absorbed. For photons with an energy above the band gap energy, only a fraction of the energy above the band gap can be converted to useful output. When a photon of greater energy is absorbed, the excess energy above the band gap is converted to kinetic energy of the carrier combination. The excess kinetic energy is converted to heat through phonon interactions as the kinetic energy of the carriers slows to equilibrium velocity.

For a silicon solar cell assembly, the maximum sensitivity (because the energy band structure of the monocrystalline silicon of 1.21 eV) is at a wavelength of $\lambda=950$ nm. A monocrystalline silicon solar cell assembly is virtually non-responsive to the ultraviolet ($\lambda<400$ nm).

The '466 application describes power conversion system includes a power conversion device which produces electric power upon illumination and includes a light conversion device which down-converts and up-converts a radiant source of energy into a specific energy spectrum for the illumination of the power conversion device. The conversion element includes a first plurality of particles which upon radiation from a first radiation source radiate at a higher energy than the first radiation source, and includes a second plurality of particles which upon radiation from the first radiation source radiate at a lower energy than the first radiation source.

Here, in this invention, the above-noted energy modulation agents (and combinations thereof) would be used as the particles which upon radiation from the first radiation source radiate at a lower energy than the first radiation source. As noted above and while not bound to any particular theory, it is possible that the mechanism of emission, absorption, and re-emission within the above-noted energy modulation agents (and combinations thereof) changes the resultant spectral output. Thus, the combinations with their normally predominant emission at different distinctive wavelengths may have at least their relative strengths changed and altered (i.e., changes in extent, intensity, spectral width, etc) and can be designed to match better the solar spectrum to the spectral efficiency of a solar photoconversion cell.

Computer-Assisted Control

In one embodiment of the invention, there is provided a computer implemented system for designing and selecting suitable combinations of initiation energy source, energy modulation agent, and activatable agent. For example, the computer system 5 can include a central processing unit (CPU) having a storage medium on which is provided: a database of excitable compounds, a first computation module for a photoactivatable agent or energy transfer agent, and a second computation module predicting the requisite energy flux needed to sufficiently activate the energy transfer agent or photoactivatable agent.

Figure 4:
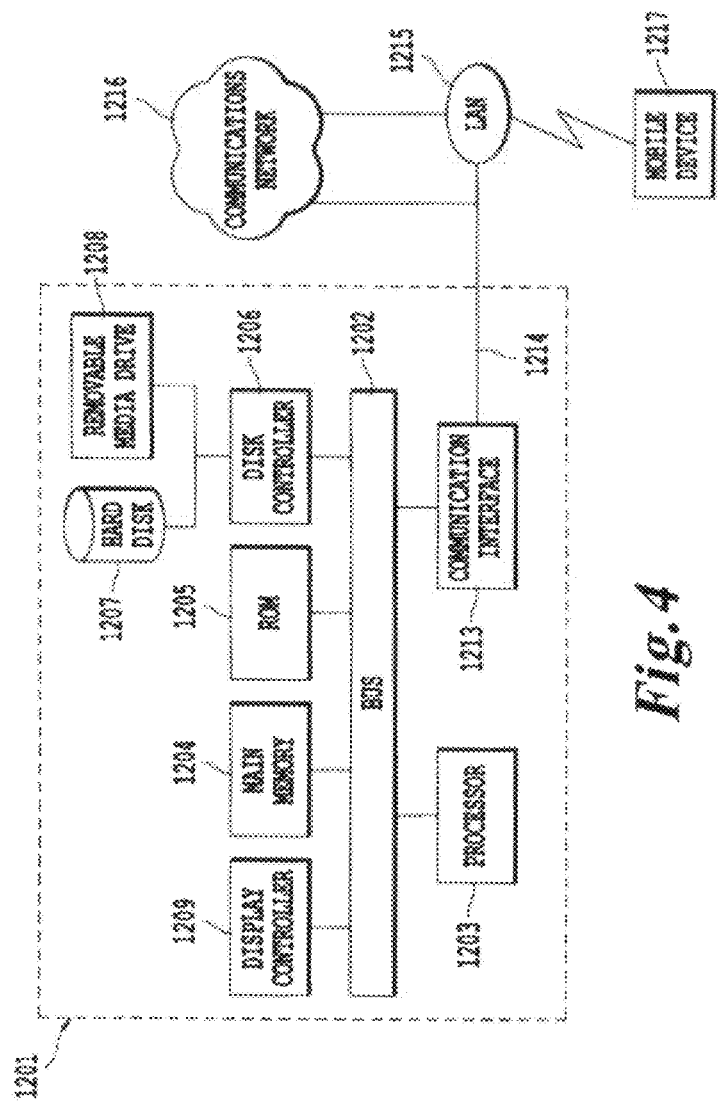
FIG. 4 illustrates an exemplary computer system for implementing various embodiments of the invention.

FIG. 4 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps (or functions) of this invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The reagents and chemicals useful for methods and systems of the invention may be packaged in kits to facilitate application of the invention. In one exemplary embodiment, a kit would comprise at least one activatable agent capable of producing a predetermined cellular change, at least one energy modulation agent capable of activating the at least one activatable agent when energized, optionally at least one plasmonics agent that can enhance applied initiation energy such that the enhanced initiation energy activates the at least one activatable agent which produces a change in the medium when activated, and containers suitable for storing the various agents in stable form, and further comprising instructions for administering the at least one activatable agent and/or at least one energy modulation agent to a medium, and for applying an initiation energy from an initiation energy source to activate the activatable agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

System Implementation

In one embodiment of the invention, there is provided a first system for producing a change in a medium (which may or may not to be disposed in an artificial container). The first system includes a mechanism configured to supply in the medium at least one of a plasmonics agent and an energy modulation agent (down converters, mixtures of down converters, up converters, mixtures of up converters, and combinations thereof). The plasmonics agent enhances or modifies energy in a vicinity of itself. In one example, the plasmonics agent enhances or modifies the applied initiation energy such that the enhanced initiation energy produces directly or indirectly the change in the medium. The system includes an initiation energy source configured to apply an initiation energy through the artificial container to the medium to activate the at least one activatable agent in the medium.

In one embodiment, the applied initiation energy interacts with the energy modulation agent to directly or indirectly produce the change in the medium by emitted light (UV and/or visible light). The energy modulation agent predominantly emits light in a visible wavelength range to activate a normally ultraviolet activated photoreaction to produce said change.

Viewed differently, the energy modulation agent has a normal predominant emission of radiation in a first wavelength range (WR1) outside of a second wavelength range (WR2) known to produce a change. However, under exposure to the applied initiation energy, the produces the change directly or indirectly.

In one embodiment, the normal predominant emission of the energy modulation agent is in the visible-light wavelength range, and the wavelength range WR2 is in the ultraviolet range. In one embodiment, the normal predominant emission of the energy modulation agent is characterized by visible emissions in at least one of the red, yellow, green, blue, and not in the ultraviolet range. In one embodiment, the energy modulation agent emits radiation in WR2. In one embodiment, the energy modulation agent emits radiation in the ultraviolet range.

As used herein, "predominantly" means that the intensity of light in the visible wavelength range (400 nm to 680 nm) is at least two to three times greater than light in the ultraviolet range (300 to 400 nm).

As used herein, "normal predominant emission" means the emission that an energy modulation agent is normally expected to emit upon application of an initiation energy. For example, the red, flamingo, yellow, green, blue phosphors noted above are normally expected to emit predominantly in those wavelength ranges indicative of the name when activated for example by UV light, x-ray, or electron beam. Other energy modulation agents for example upconverters might also be expected to normally emit predominantly in the visible wavelength with no expected UV component.

In this invention, use of such energy modulation agents with a "normal predominant emission" in a first wavelength range (WR1) outside of a second wavelength range (WR2) known to produce a change in a medium, under exposure to appropriately selected initiation energy produces changes in a medium or body normally expected to occur only with the second wavelength range WR2.

In one embodiment, the energy modulation agent converts the applied initiation energy and produces light (UV and/or visible light) at an energy different from the applied initiation energy. The plasmonics agent (if present) can enhance the light from the at least one energy modulation agent. In one embodiment, the applied initiation energy source is an external initiation energy source. In one embodiment, the applied initiation energy source is a source that is at least partially in a container holding the medium.

The medium in one embodiment is substantially transparent to the initiation energy. For example, if the medium is a liquid or fluid food product such as orange juice which has a substantial amount of suspended solids, then UV light for example as described above and even visible light will be substantially absorbed and/or scattered by the orange juice medium. Furthermore, microwave energy will likewise be absorbed by this medium. However, an initiation energy source such as an X-ray source will essentially transmit entirely through for example an orange juice medium. The effect is the medium can now be totally illuminated with the external initiation energy source.

Other sources and tuned to specific wavelengths may also be used as the initiation energy source. These sources would take advantage of an "optical window" in the medium where for example a particular wavelength of light would not be absorbed. Water selectively scatters and absorbs certain wavelengths of visible light. The long wavelengths of the light spectrum—red, yellow, and orange—can penetrate to approximately 15, 30, and 50 meters (49, 98, and 164 feet), respectively, while the short wavelengths of the light spectrum—violet, blue and green—can penetrate further. Thus, for many aqueous based systems, non-high energy X-ray sources may not be needed. In those situations, energy modulation agents and plasmonics agents would be added whose interaction with the emitted light from the energy modulation agents (UV and/or visible light) would produce for example photoactivation of catalysts in the aqueous medium. Light produced from the energy modulation agents can also be enhanced by the plasmonics agents in the medium.

Accordingly, depending on the medium and the energy modulation agent and the activatable agent, the initiation energy source can include at least one of an X-ray source, a gamma ray source, and/or an electron beam source. The initiation energy source can then be an energy source emitting a wavelength whose depth of penetration penetrates throughout the medium. The initiation energy in one embodiment may be scattered or absorbed in the medium, but the plasmonics agents make useful the remnant light. The medium to be effected can be a medium to be fermented, sterilized, or cold pasteurized. The medium to be effected can include bacteria, viruses, yeasts, and fungi.

The activatable agents can be photoactivatable agents such as the photocages (described elsewhere) such that upon exposure to the initiation energy source, the photocage disassociates rendering an active agent available.

Indeed, as described above, photocages nominally considered breakable only by UV-activated processes can be broken open by the down converters, mixtures of down converters, up converters, mixtures of up converters, and combinations thereof which normally would not be expected to generate sufficient UV light for photocage breakage.

The activatable agents can include agents such as psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. The activatable agents can include photocatalysts such as $TiO_2$, ZnO, CdS, CdSe, $SnO_2$, $SrTiO_3$, $WO_3$, $Fe_2O_3$, and $Ta_2O_5$ particles.

The first system can include a mechanism configured to provide in the medium energy modulation agents (down converters, mixtures of down converters, up converters, mixtures of up converters, and combinations thereof) which converts the initiation energy to an activation energy for activation of the activatable agent(s). Phosphorescent compounds, chemiluminescent compounds, and bioluminescent compounds can be included in a photocage. The energy modulation agent(s) can be up conversion or down conversion agents. The energy modulation agent(s) can be luminescent particles which emit light upon exposure to said initiation energy. The luminescent particles can be nanoparticles of semiconducting or metallic materials. The luminescent particles can be chemiluminescent particles which show enhanced chemiluminescence upon exposure to microwaves.

The first system can include a mechanism configured to provide in the medium plasmonics-agents including metal nanostructures such as for example nanospheres, nanorods, nanocubes, nanopyramids, nanoshells, multi-layer nanoshells, and combinations thereof. The form and structure of these plasmonics-agents can vary as shown in the figure above.

Depending on the initiation energy source, the system can include a container for the medium that is permeable to the applied initiation energy. For example, for an X-ray source, the container can be made of aluminum, quartz, glass, or plastic. Furthermore, the container can be a container which receives and transmits the initiation energy to fluid products to pasteurize the fluid products, or can be a container which receives and transmits the initiation energy to fluid products to remediate contaminants in the fluid products.

In another embodiment of the invention, there is provided a second system for curing a radiation-curable medium. The second system includes a mechanism configured to supply an uncured radiation-curable medium including at least one plasmonics agent, energy modulation agents (down converters, mixtures of down converters, up converters, mixtures of up converters, and combinations thereof), and at least one activatable agent which produces a change in the radiation-curable medium when activated, and further includes an applied initiation energy source configured to apply initiation energy to a composition including the uncured radiation-curable medium, optionally the plasmonics agent, and the energy modulation agent. The energy modulation agents as described above absorb the initiation energy and convert the initiation energy to an activation energy capable of curing the uncured medium (i.e., promoting polymerization of polymers in the uncured medium). The plasmonics agent enhances the applied initiation energy such that the enhanced initiation energy directly or indirectly cures the medium by polymerization of polymers in the medium. For example, the plasmonics agent can enhance the activation energy light such that enhanced light activates the at least one photoactivatable agent to polymerize polymers in the medium. In another example, activation of the energy modulation agent produces radiation (such as, for example, UV and/or visible light) which activates the at least one photoactivatable agent to polymerize polymers in the medium.

The second system has attributes similar to the first system described above and can further permit the at least one activatable agent to include a photoinitiator such as one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

The second system can also include a mechanism configured to provide in the medium plasmonics-agents including metal nanostructures such as for example nanospheres, nanorods, nanocubes, nanopyramids, nanoshells, multi-layer nanoshells, and combinations thereof.

The second system can include a container for the uncured radiation-curable medium that is permeable to the applied initiation energy. The container can be configured to contain the uncured radiation-curable medium or to hold a mold of the uncured radiation-curable medium. The container as before can be an aluminum container, a quartz container, a glass container, or a plastic container, depending on the applied initiation energy.

In one embodiment, an energy source (e.g., an external energy source) is configured to irradiate the uncured radiation-curable medium in a joint region (or regions) adhering one region of a utensil to another region of the utensil. In another embodiment, the energy source is configured to irradiate the joint regions and thereby induce sterilization of the joint regions due to the production of internal radiation (UV and/or visible light) inside the joint regions. In another embodiment, the energy source is configured to irradiate a surface coating. In another embodiment, the energy source is configured to irradiate a mold of the radiation-curable medium.

The radiation-curable medium in the surface coating or in the mold or in other medium can include color pigments to add color to a finished cured product. The radiation-curable medium in the surface coating or in the mold or in another medium can include fumed silica to promote strength and enhance distribution of the internally generated radiation (UV and/or visible light). The radiation-curable medium in the surface coating or in the mold or in another medium can include a moisture cure promoter to supplement the cure.

The second system provides one mechanism for production of novel radiation-cured articles, which include a radiation-cured medium, optionally at least one plasmonics agent, and at least one energy modulation agent distributed throughout the medium. The energy modulation agents (down converters, mixtures of down converters, up converters, mixtures of up converters, and combinations thereof) being substances which is capable of converting an applied energy to a radiation (UV and/or visible light) capable of producing a cure for the radiation-cured medium. The plasmonics agent enhances the applied initiation energy such that the enhanced initiation energy activates the energy modulation agents.

Radiation produced from the energy modulation agent can also be enhanced by the plasmonics agents in the medium. The article can include luminescent particles such as for example nanotubes, nanoparticles, chemilumiscent particles, and bioluminescent particles, and mixtures thereof. The article can include nanoparticles of semiconducting or metallic materials. The article can include chemiluminescent particles. The article can include color pigments or fumed silica. The article can include plasmonics-agents including metal nanostructures such as for example nanospheres, nanorods, nanocubes, nanopyramids, nanoshells, multi-layer nanoshells, and combinations thereof. The form and structure of these plasmonics-agents can include the probe structures detailed above.

In another embodiment of the invention, there is provided a third system for producing a change in a medium disposed in an artificial container. The third system includes a mechanism configured to provide to the medium 1) an activatable agent and 2) at least one of a plasmonics agent and various energy modulation agents (down converters, mixtures of down converters, up converters, mixtures of up converters, and combinations thereof). The energy modulation agent converts an initiation energy to an activation energy (UV and/or visible light) which then activates the at least one activatable agent. The third system further includes an applied initiation energy source configured to apply the initiation energy through the artificial container to activate the at least one activatable agent in the medium. The plasmonics agent enhances or modifies an energy in a vicinity of itself. In one example, the plasmonics agent enhances or modifies the applied initiation energy such that the enhanced initiation energy produces directly or indirectly the change in the medium.

The third system has similar attributes to the first and second systems described above, and further includes encapsulated structures including at least one of the energy modulation agents and the plasmonics agents. The encapsulated structures can include nanoparticles of the energy modulation agents (down converters, mixtures of down converters, up converters, mixtures of up converters, and combinations thereof) encapsulated with a passivation layer or can include sealed quartz or glass tubes having the energy modulation agent inside. The encapsulated structures can include sealed tubes having the plasmonics agent disposed on an outside of the sealed tube (which may or may not be exposed directly to the medium).

In another embodiment of the invention, there is provided a fourth system for producing a photo-stimulated change in a medium disposed in an artificial container. The fourth system includes a mechanism configured to provide in the medium at least one of a plasmonics agent and various energy modulation agents (down converters, mixtures of down converters, up converters, mixtures of up converters, and combinations thereof). The energy modulation agents convert an initiation energy to an activation energy (UV and/or visible light) which then produces the photo-stimulated change. The fourth system further includes an initiation energy source configured to apply the initiation energy to the medium to activate the at least one energy modulation agent in the medium. The plasmonics agent enhances or modifies an energy in a vicinity of itself. In one example, the plasmonics agent enhances or modifies the applied initiation energy such that the enhanced initiation energy produces directly or indirectly the change in the medium. The system can include encapsulated structures including therein the energy modulation agents (down converters, mixtures of down converters, up converters, mixtures of up converters, and combinations thereof). The encapsulated structures can include nanoparticles of the energy modulation agent encapsulated with a passivation layer. The encapsulated structures can include sealed tubes having the plasmonics agent disposed on an outside of the sealed tube (which may or may not be exposed directly to the medium).

The fourth system can include a container which receives and transmits the initiation energy to products within the medium. The products can include plastics, where the activation energy alters the surface structure of the plastics. The products can include polylactic acid (PLA) plastics and polyhydroxyalkanoates (PHA) plastics. In this embodiment, the activation energy can photo-graft a molecular species onto a surface of the plastics.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A method for producing a change in a medium or body, comprising:
   (1) placing in a vicinity of the medium or body at least one energy modulation agent configured to emit radiation into the medium or body upon interaction with an initiation energy; and
   (2) applying the initiation energy from an energy source to the medium or body,
   wherein the applied initiation energy interacts with the energy modulation agent to directly or indirectly produce the change in the medium or body by said emitted radiation, and
   wherein said energy modulation agent has a normal predominant emission of radiation in a first wavelength range (WR1) outside of a second wavelength range (WR2) known to produce said change, but under exposure to said applied initiation energy produces said change.

2. The method of claim 1, wherein the normal predominant emission of the energy modulation agent is in the visible-light wavelength range and said wavelength range WR2 is in the ultraviolet range.

3. The method of claim 2, wherein the normal predominant emission of the energy modulation agent is characterized by visible emissions in at least one of the red, yellow, orange, green, blue, and not in the ultraviolet range.

4. The method of claim 2, wherein the energy modulation agent emits said radiation in WR2.

5. The method of claim 4, wherein the energy modulation agent emits said radiation in the ultraviolet range.

6. The method of claim 1, wherein the energy modulation agent comprises at least one phosphor or a combination of two or more phosphors.

7. The method of claim 6, wherein the energy modulation agent comprises a mixture of three phosphors.

8. The method of claim 1, further comprising a plasmonics agent configured to 1) enhance or modify said light from the energy modulation agent or 2) enhance or modify the initiation energy.

9. The method of claim 1, wherein applying comprises applying the initiation energy to activate a photoactivatable agent.

10. The method of claim 9, wherein the photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

11. The method of claim 10, wherein the photoactivatable agent comprises a photocaged drug, a psoralen, a coumarin, or a derivative thereof.

12. The method of claim 11, wherein at least one of a cancer cell, a tumor cell, an autoimmune disorder, a virus, or a blood-borne germicide is treated by the photocaged drug, the psoralen, the coumarin, or the derivative thereof.

13. The method of claim 1, wherein the change produced is treatment of a cell proliferation disorder in a subject in need thereof.

14. The method of claim 1, wherein applying comprises:
   applying the initiation energy to an uncured radiation-curable medium to thereby cure the uncured radiation-curable medium;
   applying the initiation energy to a structure prefilled with an uncured radiation-curable medium to thereby cure the uncured radiation-curable medium; or
   applying the initiation energy to produce a cured element from the uncured radiation-curable medium.

15. The method of claim 1, wherein applying comprises applying said initiation energy from a source emitting at least one of x-rays, gamma rays, and an electron beam.

16. The method of claim 1, further comprising a plasmonics agent including a metallic structure.

17. The method of claim 16, wherein the metallic structure comprises at least one of nanospheres, nanorods, nanocubes, nanopyramids, nanoshells, multi-layer nanoshells, and combinations thereof.

18. The method of claim 1, wherein the energy modulation agent comprises at least one of a sulfide, a telluride, a selenide and an oxide semiconductor and a combination thereof.

19. The method of claim 1, wherein the energy modulation agent comprises at least one of $CaWO_4:Pb^{2+}$, $CaWO_4:W$, $Sr_3(PO_4)_2:Eu^{2+}$, $Ba_3(PO_4)_2:Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4:Mn^{2+}$, $Y_3(Al,Ga)_5O_{12}:Ce^{3+}$, $BaMg_2Al_{14}O_{24}:Mn^{2+}$, $BaMgAl_{14}O_{23}:Mn^{2+}$, $SrAl_{12}SiO_{19}:Mn^{2+}$, $ZnAl_{12}O_{19}:Mn^{2+}$, $CaAl_{12}O_{19}:Mn^{2+}$, $YBO_3:Tb^{3+}$, $Sr_4Si_3O_8Cl_4:Eu^{3+}$, $Y_2O_3:Eu^{3+}$, $Y_2SiO_5:Eu^{3+}$, $Y_3Al_5O_{12}:Eu^{3+}$, $CaSiO_3:Mn^{2+}$, and $YVO_4:Eu^{3+}$.

20. The method of claim 1, further comprising:
a plasmonics agent comprising a dielectric-metal composite; or
a plasmonics agent comprising a plurality of differently sized metal particles disposed in vicinity of each other as a composite plasmonics agent.

21. The method of claim 1, wherein the change in the medium comprises a change in organism activity.

22. The method of claim 21, wherein the change in activity comprises at least one of a sterilization of the medium or a deactivation of fermentation in the medium.

23. The method of claim 21, wherein the change in activity comprises a cold pasteurization of the medium.

24. The method of claim 1, wherein applying comprises sterilizing a medium including at least one organism selected from the group consisting of bacteria, viruses, yeasts, and fungi.

25. The method of claim 1, further comprising introducing a photoactivatable agent to the medium.

26. The method of claim 25, wherein the photoactivatable agent comprises an active agent contained within a photocage, configured such that upon exposure to said emitted radiation, the photocage releases the active agent into the medium.

27. The method of claim 25, wherein the photoactivatable agent comprises a photocatalyst.

28. The method of claim 27, wherein the photocatalyst agent comprises at least one of $TiO_2$, $ZnO$, $CdS$, $CdSe$, $SnO_2$, $SrTiO_3$, $WO_3$, $Fe_2O_3$, and $Ta_2O_5$.

29. The method of claim 1, wherein applying comprises:
applying the initiation energy throughout an entire volume of an artificial container.

30. The method of claim 29, wherein applying comprises:
transmitting the initiation energy through said artificial container comprising at least one of an aluminum container, a quartz container, a glass container, a plastic container or a combination thereof.

31. The method of claim 1, wherein the energy modulation agent is provided within the medium at a density where said emitted radiation generated in the medium from the energy modulation agent is not occluded throughout the medium.

32. The method of claim 1, further comprising providing segregated within the medium the energy modulation agent.

33. The method of claim 32, wherein providing segregated within the medium comprises providing encapsulations of the energy modulation agent in the medium.

34. The method of claim 33, wherein providing encapsulations comprises providing said encapsulations at a density where the emitted radiation is not occluded throughout the medium.

35. The method of claim 1, wherein applying comprises applying the initiation energy to waste water to reduce contaminants in the waste water.

36. The method of claim 1, wherein applying comprises sterilizing parts of the medium or body.

37. The method of claim 1, wherein applying comprises applying the initiation energy to fluids to sterilize the fluids.

38. The method of claim 37, wherein applying comprises at least one of:
sterilizing blood products or food products; or
pasteurizing the fluids or the food products.

39. The method of claim 1, wherein applying comprises applying the initiation energy to alter a surface structure of an article in the medium or photo-graft a molecular species onto the surface of the article.

40. The method of claim 1, wherein applying produces a color change or color enhancement in the medium.

41. The method of claim 1, wherein applying comprises applying the initiation energy at a first dose level to cause an interim change and subsequently applying the initiation energy at a second dose level cause said change in the medium or body.

42. A method for curing of a radiation-curable medium, comprising:
applying an initiation energy throughout a composition comprising 1) an uncured radiation-curable medium and 2) at least one energy modulation agent, wherein the initiation energy interacts with the energy modulation agent to directly or indirectly cure the uncured medium by polymerization of polymers in the medium; and
curing the radiation-curable medium by activating a photoinitiator in the radiation-curable medium,
wherein said energy modulation agent has a normal predominant emission of radiation in a first wavelength range (WR1) outside of a second wavelength range (WR2) known to activate the photoinitiator, but under exposure to said applied initiation energy cures the medium.

43. The method of claim 42, wherein the normal predominant emission of the energy modulation agent is in the visible-light wavelength range and said wavelength range WR2 is in the ultraviolet range.

44. The method of claim 42, wherein the normal predominant emission of the energy modulation agent is characterized by visible emissions in at least one of the red, yellow, green, blue, and not in the ultraviolet range.

45. The method of claim 44, wherein the energy modulation agent emits said radiation in the ultraviolet range.

46. The method of claim 42, wherein the energy modulation agent emits said radiation in WR2.

47. A system for producing a change in a medium disposed in an artificial container, comprising:
a mechanism configured to provide to the medium 1) an activatable agent and 2) at least one energy modulation agent, said energy modulation agent is configured to emit light into the medium upon interaction with an initiation energy; and
an initiation energy source configured to apply the initiation energy to the medium,
wherein said energy modulation agent has a normal predominant emission of radiation in a first wavelength range (WR1) outside of a second wavelength range (WR2) known to produce said change, but under exposure to said applied initiation energy produces said change.

48. The system of claim 47, wherein the normal predominant emission of the energy modulation agent is in the visible-light wavelength range and said wavelength range WR2 is in the ultraviolet range.

49. The system of claim 47, wherein the normal predominant emission of the energy modulation agent is characterized by visible emissions in at least one of the red, yellow, orange, green, blue, and not in the ultraviolet range.

50. The system of claim 49, wherein the energy modulation agent emits said radiation in the ultraviolet range.

51. The system of claim 47, wherein the energy modulation agent emits said radiation in WR2.

52. A system for curing of a radiation-curable medium, comprising:
 a mechanism configured to supply an uncured radiation-curable medium including an activatable agent and at least one energy modulation agent into the uncured radiation-curable medium; and
 an initiation energy source configured to apply an initiation energy throughout a region including the uncured radiation-curable medium,
 wherein said energy modulation agent has a normal predominant emission of radiation in a first wavelength range (WR1) outside of a second wavelength range (WR2) known to produce said curing, but under exposure to said applied initiation energy produces said curing.

53. The system of claim 52, wherein the normal predominant emission of the energy modulation agent is in the visible-light wavelength range and said wavelength range WR2 is in the ultraviolet range.

54. The system of claim 52, wherein the normal predominant emission of the energy modulation agent is characterized by visible emissions in at least one of the red, yellow, green, blue, and not in the ultraviolet range.

55. The system of claim 54, wherein the energy modulation agent emits said radiation in the ultraviolet range.

56. The system of claim 52, wherein the energy modulation agent emits said radiation in WR2.

57. A radiation-curable article, comprising:
 a radiation-curable medium; and
 at least one energy modulation agent distributed throughout the medium;
 said energy modulation agent being a substance which is capable of converting initiation energy to a light capable of curing the radiation-curable medium by polymerization of polymers in the radiation-curable medium,
 wherein said energy modulation agent has a normal predominant emission of radiation in a first wavelength range (WR1) outside of a second wavelength range (WR2) known to cure the radiation-curable medium, but under exposure to said initiation energy cures the radiation-curable medium.

58. The article of claim 57, wherein the normal predominant emission of the energy modulation agent is in the visible-light wavelength range and said wavelength range WR2 is in the ultraviolet range.

59. The article of claim 57, wherein the normal predominant emission of the energy modulation agent is characterized by visible emissions in at least one of the red, yellow, orange, green, blue, and not in the ultraviolet range.

60. The article of claim 59, wherein the energy modulation agent emits said radiation in the ultraviolet range.

61. The article of claim 57, wherein the energy modulation agent emits said radiation in WR2.

62. A method for producing a cured element inside a structure, comprising:
 (1) placing inside the structure a radiation curable medium including at least one energy modulation agent, said energy modulation agent is configured to emit light into the medium upon interaction with an initiation energy; and
 (2) applying to the medium said initiation energy from a directed or focused energy source,
 wherein said energy modulation agent has a normal predominant emission of radiation in a first wavelength range (WR1) outside of a second wavelength range (WR2) known to cure the radiation curable medium, but under exposure to said applied initiation energy cures the radiation curable medium and produces the cured element inside the structure.

63. The method of claim 62, wherein the normal predominant emission of the energy modulation agent is in the visible-light wavelength range and said wavelength range WR2 is in the ultraviolet range.

64. The method of claim 62, wherein the normal predominant emission of the energy modulation agent is characterized by visible emissions in at least one of the red, yellow, orange, green, blue, and not in the ultraviolet range.

65. The method of claim 64, wherein the energy modulation agent emits said radiation in the ultraviolet range.

66. The method of claim 62, wherein the energy modulation agent emits said radiation in WR2.

* * * * *